(12) United States Patent
Yang et al.

(10) Patent No.: US 9,642,933 B2
(45) Date of Patent: May 9, 2017

(54) COMPOSITIONS COMPRISING BIOADHESIVES AND METHODS OF MAKING THE SAME

(71) Applicant: The Board of Regents, The University of Texas System, Austin, TX (US)

(72) Inventors: Jian Yang, State College, PA (US); Mohammadreza Mehdizadeh, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 160 days.

(21) Appl. No.: 13/753,683

(22) Filed: Jan. 30, 2013

(65) Prior Publication Data

US 2013/0217790 A1 Aug. 22, 2013

Related U.S. Application Data

(60) Provisional application No. 61/592,041, filed on Jan. 30, 2012.

(51) Int. Cl.
*A61L 24/04* (2006.01)
*C08G 63/685* (2006.01)
(Continued)

(52) U.S. Cl.
CPC ......... *A61L 24/046* (2013.01); *A61L 24/0031* (2013.01); *A61L 24/0042* (2013.01);
(Continued)

(58) Field of Classification Search
None
See application file for complete search history.

(56) References Cited

U.S. PATENT DOCUMENTS 5,480,963 A 1/1996 Jiang et al.
8,148,569 B1 4/2012 O'Lenick et al.
(Continued)

FOREIGN PATENT DOCUMENTS

WO    WO 96 02276    * 2/1996
WO    WO-96/02276 A2    2/1996
(Continued)

OTHER PUBLICATIONS

Tatooles, CJ et al., The use of crosslinked gelatin as a tissue adhesive to control hemorrhage from liver and kidney, Surgery, 60(4): pp. 857-861, (1966).
(Continued)

*Primary Examiner* — Bethany Barham
*Assistant Examiner* — Domonic Lazaro
(74) *Attorney, Agent, or Firm* — McCarter & English, LLP

(57) ABSTRACT

In one aspect, compositions are described herein. In some embodiments, a composition comprises a polymer or oligomer formed from one or more polycarboxylic acids, one or more alcohols, and one or more catechol-containing species. In another aspect, methods of making a composition are described herein. In some embodiments, a method of making a composition comprises providing a polycarboxylic acid; providing an alcohol; combining the polycarboxylic acid with the alcohol; adding a catechol-containing species to the combination of the polycarboxylic acid and the alcohol; and forming a polymer or oligomer from the polycarboxylic acid, the alcohol, and the catechol-containing species. In some embodiments, the catechol-containing species comprises an amine moiety, a carboxylic acid moiety, or a hydroxyl moiety that is not part of the catechol group.

24 Claims, 24 Drawing Sheets

(51) Int. Cl.
| | |
|---|---|
| *C08G 63/668* | (2006.01) |
| *A61L 27/52* | (2006.01) |
| *A61L 27/58* | (2006.01) |
| *A61L 24/00* | (2006.01) |

(52) U.S. Cl.
CPC .............. *A61L 27/52* (2013.01); *A61L 27/58* (2013.01); *C08G 63/668* (2013.01); *C08G 63/6854* (2013.01); *A61L 2400/12* (2013.01)

(56) References Cited

U.S. PATENT DOCUMENTS

| | | | |
|---|---|---|---|
| 8,192,726 | B1 | 6/2012 | O'Lenick et al. |
| 8,277,787 | B1 | 10/2012 | O'Lenick et al. |
| 2002/0082694 | A1 | 6/2002 | McKay |
| 2003/0180344 | A1 | 9/2003 | Wise et al. |
| 2003/0185752 | A1 | 10/2003 | Nathan et al. |
| 2003/0185871 | A1 | 10/2003 | Nathan et al. |
| 2004/0120981 | A1 | 6/2004 | Nathan |
| 2004/0122205 | A1 | 6/2004 | Nathan |
| 2004/0253203 | A1 | 12/2004 | Hossainy et al. |
| 2005/0063939 | A1 | 3/2005 | Ameer et al. |
| 2007/0071790 | A1 | 3/2007 | Ameer et al. |
| 2008/0086199 | A1 | 4/2008 | Dave et al. |
| 2008/0262613 | A1 | 10/2008 | Gogolewski |
| 2009/0093565 | A1 | 4/2009 | Yang et al. |
| 2009/0148945 | A1 | 6/2009 | Ameer et al. |
| 2009/0325859 | A1 | 12/2009 | Ameer et al. |
| 2010/0036476 | A1 | 2/2010 | Ameer et al. |
| 2010/0076162 | A1 | 3/2010 | Ameer et al. |
| 2011/0008277 | A1 | 1/2011 | Bruggeman et al. |
| 2011/0071079 | A1 | 3/2011 | Ameer et al. |
| 2011/0124765 | A1 | 5/2011 | Yang et al. |
| 2011/0142790 | A1 | 6/2011 | Chen |
| 2011/0159113 | A1 | 6/2011 | Adeli et al. |
| 2011/0183435 | A1 | 7/2011 | Yang et al. |
| 2011/0280937 | A1 | 11/2011 | Moriuchi et al. |
| 2012/0053303 | A1 | 3/2012 | Djuric et al. |
| 2012/0136088 | A1 | 5/2012 | Aizawa et al. |
| 2012/0225972 | A1 | 9/2012 | Ameer et al. |
| 2012/0237443 | A1 | 9/2012 | Ameer et al. |
| 2012/0238521 | A1 | 9/2012 | Sun et al. |
| 2012/0244108 | A1 | 9/2012 | Yang et al. |
| 2012/0322155 | A1 | 12/2012 | Ameer et al. |

FOREIGN PATENT DOCUMENTS

| | | |
|---|---|---|
| WO | WO 2009137715 A2 * | 11/2009 |
| WO | WO-2011/130539 A2 | 10/2011 |

OTHER PUBLICATIONS

Bonchek, LI et al., Experimental evaluation of a cross-linked gelatin adhesive in gastrointestinal surgery, Ann Surg, 165(3): pp. 420-424, (1967).
Bonchek, LI et al., Use of a cross-linked gelatin tissue adhesive in surgery of the urinary tract, Surg Gynecol Obstet, 125(6): pp. 1301-1306, (1967).
Graham, DG et al., the role of 2,4,5-trihydroxphenylalanine in melanin biosynthesis, J Biol Chem, 252(16): pp. 5729-5734, (1977).
Staindl, O, Tissue adhesion with highly concentrated human fibrinogen in otolaryngology, Ann Otol Rhinol Laryngol, 88(3 Pt 1): pp. 413-418, (1979).
Waite, JH et al., the bioadhesive of Mytilus byssus: a protein containing L-dopa, Biochem Biophys Res Commun, 96(4): pp. 1554-1561, (1980).
Forrest, RD, Early history of wound treatment, J. R. Soc. Med., 75(3): pp. 198-205, (1982).
Koveker, G, Clinical application of fibrin glue in cardiovascular surgery, Thorac Cardiovasc Surg, 30(4): pp. 228-229, (1982).
Stark, J. et al., Experience with fibrin seal (Tissel) in operations for congenital heart defects, Ann Thorac Surg, 38(4): pp. 411-413, (1984).
Jorgensen, PH et al., Mechanical strength in rat skin incisional wounds treated with fibrin sealant, J Surg Res, 42(3): pp. 237-241, (1987).
Waite, JH, Nature's underwater adhesive specialist, Int J Adhesion and Adhesives, 7(1): pp. 9-14, (1987).
Gauthier, L. et al., Use of fibrin glue (Tissucol) for treating perforated or pre-perforated corneal ulcer, J Fr Ophtalmol, 12(6-7): pp. 469-476, (1989).
Rousou, J. et al., Randomized clinical trial of fibrin sealant in patients undergoing resternotomy or reoperation after cardiac operations. A multicenter study, J Thorac Cardiovasc Surg, 97(2): pp. 194-203, (1989).
Shaffrey, CI et al., Neurosurgical applications of fibrin glue: augmentation of dural closure in 134 patients, Neurosurgery, 26(2): pp. 207-210, (1990).
Strausber, RL et al., Protein-based medical adhesives, Trends Biotechnol, 8(2): pp. 53-57, (1990).
Waite, JH, The phylogeny and chemical diversity of quinone-tanned glues and varnishes, Comp Biochem Physiol B, 97(1): pp. 19-29, (1990).
Brennan, M., Fibrin glue, Blood Rev, 5(4): pp. 240-244, (1991).
Albes JM, et al., Biophysical properties of the gelatin-resorcin-formaldehyde/glutaraldehyde adhesive, Ann Thorac Surg, 56(4): pp. 910-915, (1993).
Sierra, DH, Fibrin sealant adhesive systems: a review of their chemistry, material properties and clinical applications, J Biomater Appl, 7(4): pp. 309-352, (1993).
Ennker, J. et al., the impact of gelatin-resorcinol glue on aortic tissue: a histomorphologic evaluation, J Vasc Surg, 20(1): pp. 34-43, (1994).
Spotnitz, WD, Fibrin sealant in the United States: clinical use at the University of Virginia, Thromb Haemost, 74(1): pp. 482-485, (1995).
Patel MR, et al., Postoperative cerebrospinal fluid leaks of the lumbosacral spine: management with percutaneous fibrin glue, AJNR Am J Neuroradiol, 17(3): pp. 495-500, (1996).
Sierra, DH et al., Surgical adhesives and sealants: current technology and applications, Lancastrer, Pa.: Technomic Pub. Xx, p. 247, (1996).
Bachet, J. et al., The proper use of glue: a 20-year experience with the GRF glue in acute aortic dissection, J Card Surg, 12(2 Suppl): pp. 243-253, (1997).
Radosevich, M. et al., Fibrin sealant: scientific rationale, production methods, properties, and current clinical use, Vox Sang, 72(3): pp. 133-143, (1997).
Ochsner, MG, Fibrin solutions to control hemorrhage in the trauma patient, J Long Term Eff Med Implants, 8(2): pp. 161-173, (1998).
Deming TJ, Mussel byssus and biomolecular materials, Curr Opin Chem Biol, 3(1): pp. 100-105, (1999).
Deming, TJ et al., Role of L-3,4-dihydroxyphenylalanine in mussel ashesive proteins, Journal of the American Chemical Society, 121(24): pp. 5825-5826, (1999).
Grotli, M. et al., Physical properties of poly(ethylene glycol) (PEG)-based resins for combinatorial solid phase organic chemistry: A comparison of PEG-cross-linked and Peg-grafted resins, Journal of Combinatorial Chemistry, 2(2): pp. 108-119, (2000).
Messersmith, PB et al., Synthesis and characterization of DOPA-PEG conjugates, Abstracts of Papers of the American Chemical Society, 219: p. U442-U442, (2000).
Xie, D. et al., Synthesis of novel compatibilizers and their application in PP/nylon-66 blends. I. Synthesis and characterization, Polymer, 41: pp. 3599-3607, (2000).
Tatehata, H. et al., Model polypeptide of mussel adhesive protein. I. Synthesis and adhesive studies of sequential polypeptides (X-Tyr-Lys)(n) and (Y-Lys)(n), Journal of Applied Polymer Science, 76(6): pp. 929-937, (2000).
Yamamoto, H. et al., Synthesis and wettability characteristics of model adhesive protein sequence inspired by a marine mussel, Biomacromolecules, 1(4): pp. 543-551, (2000).
Currie LJ, et al., The use of fibrin glue in skin grafts and tissue-engineered skin replacements: a review, Plast Reconstr Surg, 108(6): pp. 1713-1726, (2001).

(56) References Cited

OTHER PUBLICATIONS

Lee, BP et al., Enzymatic and non-enzymatic pathways to formation of DOPA-modified PEG hydrogels, Abstracts of Papers of the American Chemical Society, 222: pp. U319-U320, (2001).
Tatehata, H. et al., Tissue adhesive using synthetic model adhesive proteins inspired by the marine mussel, Journal of Adhesion Science and Technology, 15(9): pp. 1003-1013, (2001).
Waite, JH et al., Polyphosphoprotein from the adhesive pads of Mytilus edulis, Biochemistry, 40(9): pp. 2887-2893, (2001).
Messersmith, PB et al., Synthesis and gelation of DOPA-Modified poly(ethylene glycol) hydrogels, Biomacromolecules, 3(5): pp. 1038-1047, (2002).
Schenk, WG, $3^{rd}$ et al., Fibrin sealant facilitates hemostasis in arteriovenous polytetrafluoroethylene grafts for renal dialysis access, Am Surg, 68(8): pp. 728-732, (2002).
Barroso-Bujans, F. et al., Structural characterization of oligomers from the polycondensation of citric acid with ethylene glycol and long-chain aliphatic alcohols, J Appl Polym Sci, 88: pp. 302-306, (2003).
Conrad, K. et al., The use of fibrin glue in the correction of pollybeak deformity: a preliminary report, Arch Facial Plast Surg, 5(6): pp. 522-527, (2003).
Monahan, J. et al., Specificity of metal ion cross-linking in marine mussel adhesives, Chem Commun (Camb), 2003(14): pp. 1672-1673.
Oyane et al., Preparation and assessment of revised simulated body fluids, Journal of Biomedical Materials Research Part A, 65: 188-95, 2003.
Leggat, PA et al., Toxicity of cyanoacrylate adhesives and their occupational impacts for dental staff, Industrial Health, 42(2): pp. 207-211, (2004).
Ryan, BM et al., A pathophysiologic, gastroenterologic, and radiologic approach to the management of gastric varices, Gastroenterology, 126(4): pp. 1174-1189, (2004).
Quinn, JV, Tissue adhesives in clinical medicine, 2nd ed. Hamilton: BC Decker, Inc, vi, p. 183, (2005).
Smith, AM et al., Biological adhesives, Berlin; New York: Springer. Xvii, p. 284, (2006).
Traver, MA et al., New generation tissue sealants and hemostatic agents: innovative urologic applications, Rev Urol, 8(3): pp. 104-111, (2006).
Yang, J. et al., Development of aliphatic biodegradable photoluminescent polymers, Proceedings of the National Academy of Sciences of the United States of America, 106(25): pp. 10086-10091, (2009).
Yang, J. et al., Development of aliphatic biodegradable photoluminescent polymers (vol. 106, p. 10086, 2009), Proceedings of the National Academy of Sciences of the United States of America, 106(28): pp. 11818-11818, (2009).
Brubaker, CE et al., Biological performance of mussel-inspired adhesive in extrahepatic islet transplantation, Biomaterials, 31(3): pp. 420-427, (2010).
Gyawali et al., Citric acid-delivered in situ crosslinkable biodegradable polymers for cell delivery, Biomaterials, 31:9092-105, 2010.
U.S. Appl. No. 61/592,041, filed Jan. 30, 2012.

\* cited by examiner

COMPOSITIONS COMPRISING BIOADHESIVES AND METHODS OF MAKING THE SAME

CROSS REFERENCE TO RELATED APPLICATION

This application claims priority pursuant to 35 U.S.C. §119(e) to U.S. Provisional Patent Application Ser. No. 61/592,041, filed on Jan. 30, 2012, which is hereby incorporated by reference in its entirety.

STATEMENT REGARDING FEDERALLY SPONSORED RESEARCH

This invention was made with government support under contract number 0954109 awarded by the National Science Foundation. The government has certain rights in the invention.

FIELD

This invention relates to compositions comprising bioadhesives and methods of making and using bioadhesives, and, in particular, to biodegradable bioadhesives.

BACKGROUND

Bioadhesives, tissue sealants, and other agents can be used in various clinical and surgical applications to control blood loss and promote tissue healing. However, some materials provide relatively poor tissue adhesion and/or tensile strength. In addition, some materials used as bioadhesives present risks of blood-borne disease transmission and/or potential allergic reaction by the patient. Other materials can in some cases provide better tissue adhesion but biodegrade slowly or not at all. Additionally, some materials can release toxic species when biodegradation does occur. Such biodegradation profiles can lead to various clinical complications. Further, some materials cannot be used effectively for wet tissue adhesion and hemostatic applications and are instead indicated for application to a dry surgical field, substantially limiting their overall clinical utility.

Therefore, improved bioadhesives are needed that can provide superior tissue adhesion under wet or dry conditions while also exhibiting superior biodegradability, biocompatibility, and safety.

SUMMARY

In one aspect, compositions are described herein which, in some embodiments, can provide one or more advantages compared to some other compositions. For instance, in some embodiments, a composition described herein can provide a bioadhesive having superior mechanical properties, adhesion strength, adhesion kinetics, biocompatibility, biodegradability, and/or cytotoxicity. In other embodiments, a composition described herein can provide a tissue scaffold material having superior bioengineering properties, including under wet or dry conditions.

In some embodiments, a composition described herein comprises a polymer or oligomer formed from one or more polycarboxylic acids, one or more alcohols, and one or more catechol-containing species. Further, in some embodiments, a polymer or oligomer described herein is crosslinked to form a polymer network. A polymer network, in some embodiments, comprises a hydrogel. In addition, in some embodiments, a composition described herein further comprises a particulate material and/or a drug mixed with a polymer, oligomer, crosslinked polymer network, or hydrogel of the composition. Moreover, in some embodiments, a polymer, oligomer, polymer network, or hydrolgel described herein is in nanoparticulate form. In addition, in some embodiments, a polymer, oligomer, crosslinked polymer network, or hydrolgel described herein is bonded to a surface and/or adhered to biological material.

In another aspect, methods of making a composition are described herein which, in some embodiments, can provide one or more advantages compared to some other methods. For example, in some embodiments described herein, a method can provide a simpler and less expensive way to make various compositions, including various compositions comprising bioadhesives and/or tissue scaffolds. In some embodiments, a method of making a composition described herein comprises providing a polycarboxylic acid; providing an alcohol; combining the polycarboxylic acid with the alcohol; adding a catechol-containing species to the combination of the polycarboxylic acid and the alcohol; and forming a polymer or oligomer from the polycarboxylic acid, the alcohol, and the catechol-containing species. In some embodiments, the catechol-containing species comprises an amine moiety, a carboxylic acid moiety, or a hydroxyl moiety that is not part of the catechol group.

Moreover, a method described herein, in some embodiments, further comprises adding a particulate material and/or a drug to a polymer or oligomer fat ned as described herein. Additionally, in some embodiments, a method described herein further comprises crosslinking a polymer or oligomer to form a polymer network. In some embodiments, a method further comprises forming nanoparticles of a polymer network.

In yet another aspect, various applications of compositions are described herein which, in some embodiments, can provide one or more advantages. For example, in some embodiments, a composition described herein can be used in a method of adhering biological tissue, treating disease, and/or promoting biological tissue growth. In some embodiments, for instance, a method of adhering biological tissue comprises disposing a composition described herein between a first portion of biological tissue and a second portion of biological tissue and contacting the first portion of biological tissue with the second portion of biological tissue. In other embodiments, a method of treating disease comprises disposing a composition described herein in a biological compartment. In some embodiments wherein the composition comprises a drug, a method of treating disease can further comprise releasing the drug into the biological compartment. In still other embodiments, a method of promoting biological tissue growth comprises providing a scaffold comprising a composition described herein and disposing the scaffold in a tissue growth medium.

These and other embodiments are described in greater detail in the detailed description which follows.

DETAILED DESCRIPTION

Figure 1:
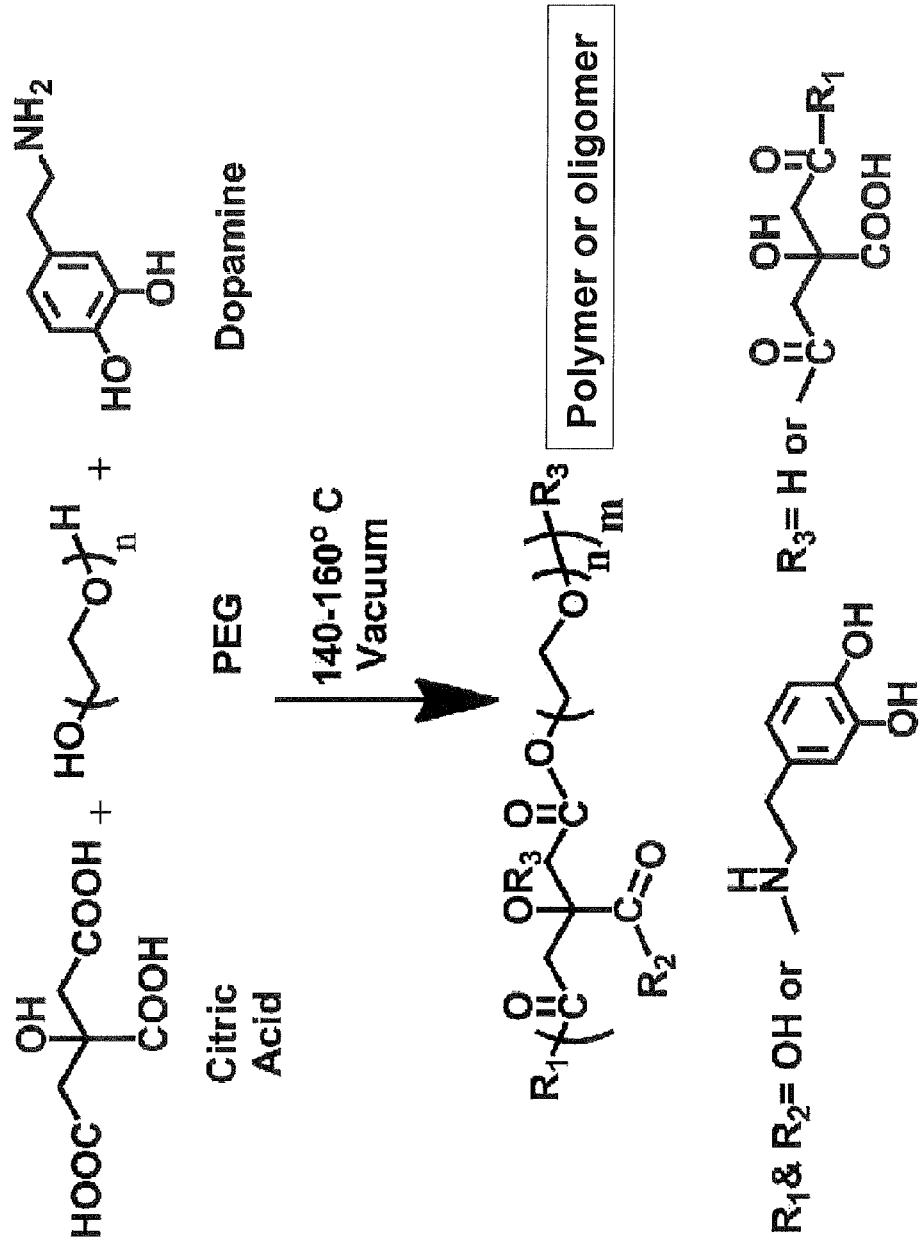
FIG. 1 illustrates a scheme of a polycondensation reaction that can be used to form a polymer or oligomer according to one embodiment described herein.

Embodiments described herein can be understood more readily by reference to the following detailed description, examples, and drawings. Elements, apparatus, and methods described herein, however, are not limited to the specific embodiments presented in the detailed description, examples, and drawings. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

I. Compositions

In one aspect, compositions are described herein. In some embodiments, a composition described herein comprises a polymer or oligomer formed from one or more polycarboxylic acids, one or more alcohols, and one or more catechol-containing species. Any polycarboxylic acid, alcohol, and catechol-containing species not inconsistent with the objectives of the present invention may be used. For example, in some embodiments, a polycarboxylic acid comprises a dicarboxylic acid. In other embodiments, a polycarboxylic acid comprises a tricarboxylic acid. In some embodiments, a polycarboxylic acid comprises citric acid. Further, in some embodiments, a polycarboxylic acid can be replaced with a corresponding methyl ester or ethyl ester of the polycarboxylic acid.

An alcohol used to form a polymer or oligomer described herein, in some embodiments, comprises a polyol. A polyol, in some embodiments, comprises an alkane diol, such as an α,ω-alkane diol, including a C2-C14 alkane diol or a C2-C6 alkane diol. In some embodiments, an alkane diol is a linear aliphatic alkane diol such as 1,4-butanediol or 1,6-hexanediol. In other embodiments, a polyol comprises an aromatic diol. In some embodiments, an alcohol comprises a poly(ethylene glycol). Any poly(ethylene glycol) not inconsistent with the objectives of the present invention may be used. In some embodiments, for instance, a poly(ethylene glycol) has a number average molecular weight between about 100 and about 5000 or between about 200 and about 1000. Further, in some embodiments, an alcohol comprises an unsaturated alcohol or an unsaturated polyol. An unsaturated alcohol, in some embodiments, comprises one or more carbon-carbon double bonds. In some embodiments, an unsaturated alcohol comprises an alkene diol.

A catechol-containing species used to form a polymer or oligomer described herein, in some embodiments, comprises at least one moiety that can form an ester or amide bond with another chemical species used to form the polymer or oligomer. For example, in some embodiments, a catechol-containing species comprises an amine moiety or a carboxylic acid moiety. Further, in some embodiments, a catechol-containing species comprises a hydroxyl moiety that is not part of the catechol moiety. In some embodiments, a catechol-containing species comprises dopamine. In some embodiments, a catechol-containing species comprises L-3,4-dihydroxyphenylalanine (L-DOPA) or D-3,4-dihydroxyphenylalanine (D-DOPA). In some embodiments, a catechol-containing species comprises 3,4-dihydroxyhydrocinnamic acid. Moreover, in some embodiments, a catechol-containing species is coupled to the backbone of the polymer or oligomer through an amide bond. In other embodiments, a catechol-containing species is coupled to the backbone of the polymer or oligomer through an ester bond.

In some embodiments, a composition described herein comprises a polymer or oligomer formed from one or more monomers of Formula (A), one or more monomers of Formula (B) or (B'), and one or more monomers of Formula (C):

(A)

-continued

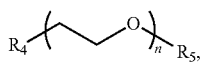
(B)

(B')

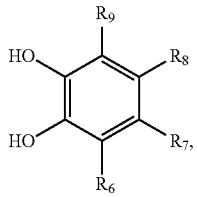
(C)

wherein $R_1$, $R_2$, and $R_3$ are independently —H, —CH$_3$, or —CH$_2$CH$_3$;
$R_4$ is —H, —OH, —OCH$_3$, —OCH$_2$CH$_3$, —CH$_3$, or —CH$_2$CH$_3$;
$R_5$ is —H, —CH$_3$, or —CH$_2$CH$_3$;
$R_6$, $R_7$, $R_8$, and $R_9$ are independently —H, —CH$_2$(CH$_2$)$_x$NH$_2$, —CH$_2$(CHR$_{10}$)NH$_2$, or —CH$_2$(CH$_2$)$_x$COOH;
$R_{10}$ is —COOH or —(CH$_2$)$_y$COOH;
n and m are independently integers ranging from 1 to 20;
x is an integer ranging from 0 to 20; and
y is an integer ranging from 1 to 20.

In some embodiments, $R_2$ is —H. Further, in some embodiments, a monomer of Formula (A) can be replaced by a polycarboxylic acid that does not have the formula of Formula (A). A polycarboxylic acid, in some embodiments, comprises a dicarboxylic acid. In some embodiments, a polycarboxylic acid comprises a tricarboxylic acid.

Further, in some embodiments, a monomer of Formula (B) or (B') can be replaced by an alcohol that does not have the formula of Formula (B) or (B'). For example, in some embodiments, an unsaturated alcohol or an unsaturated polyol can be used.

In addition, in some embodiments, three of $R_6$, $R_7$, $R_8$, and $R_9$ are —H. Further, in some embodiments, $R_6$ and $R_9$ specifically are —H. In some embodiments, a monomer of Formula (C) comprises dopamine. In some embodiments, a monomer of Formula (C) comprises L-DOPA or D-DOPA. In some embodiments, a monomer of Formula (C) comprises 3,4-dihydroxyhydrocinnamic acid. Moreover, in some embodiments, a monomer of Formula (C) is coupled to the backbone of the polymer or oligomer through an amide bond. In other embodiments, a monomer of Formula (C) is coupled to the backbone of the polymer or oligomer through an ester bond.

In some embodiments, a polymer or oligomer described herein has at least one ester bond in the backbone of the polymer or oligomer. In some embodiments, a polymer or oligomer described herein has a plurality of ester bonds in the backbone of the polymer or oligomer, such as at least three ester bonds, at least four ester bonds, or at least five ester bonds. In some embodiments, a polymer or oligomer described herein has between 2 ester bonds and 50 ester bonds in the backbone of the polymer or oligomer. Further, in some embodiments, a polymer or oligomer formed from one or more monomers of Formula (A), one or more monomers of Formula (B) or (B'), and one or more monomers of Formula (C) comprises a plurality of pendant —COOH groups, such as when $R_2$ is —H and no esterification or amidation occurs at the carboxyl group associated with $R_2$. In addition, in some embodiments, a polymer or oligomer described herein is water soluble.

In some embodiments, a polymer or oligomer of a composition described herein comprises a polymer or oligomer of Formula (I):

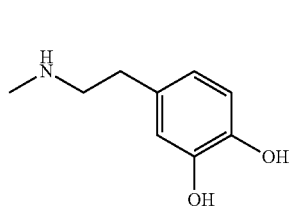
(I)

wherein $R_{11}$ and $R_{12}$ are independently

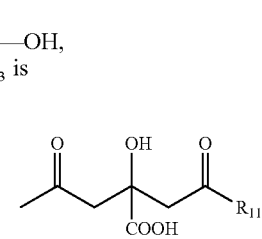

or —OH,
$R_{13}$ is

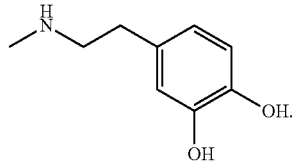

or —H,
n is an integer ranging from 1 to 20, and
m is an integer ranging from 1 to 100, provided that at least one of $R_{11}$ and $R_{12}$ is

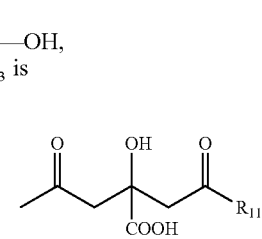

FIG. 1 illustrates a scheme of one possible polycondensation reaction that can be used to form a polymer or oligomer described herein. It should be noted that the various species used to form a polymer or oligomer described herein can be used in any combination and in any amounts or ratios not inconsistent with the objectives of the present invention. Further, in some embodiments, the identities, amounts, and/or ratios of the components of the polymer or oligomer can be selected based on a desired property of the polymer or oligomer, such as a desired solubility, biodegradability, molecular weight, catechol content, carboxylic acid content, or charge.

In addition, in some embodiments, a polymer or oligomer described herein is crosslinked to form a polymer network. A polymer network, in some embodiments, comprises a hydrogel. A hydrogel, in some embodiments, comprises an aqueous continuous phase and a polymeric disperse or discontinuous phase. Further, in some embodiments, a crosslinked polymer network described herein is not water soluble.

Figure 2:
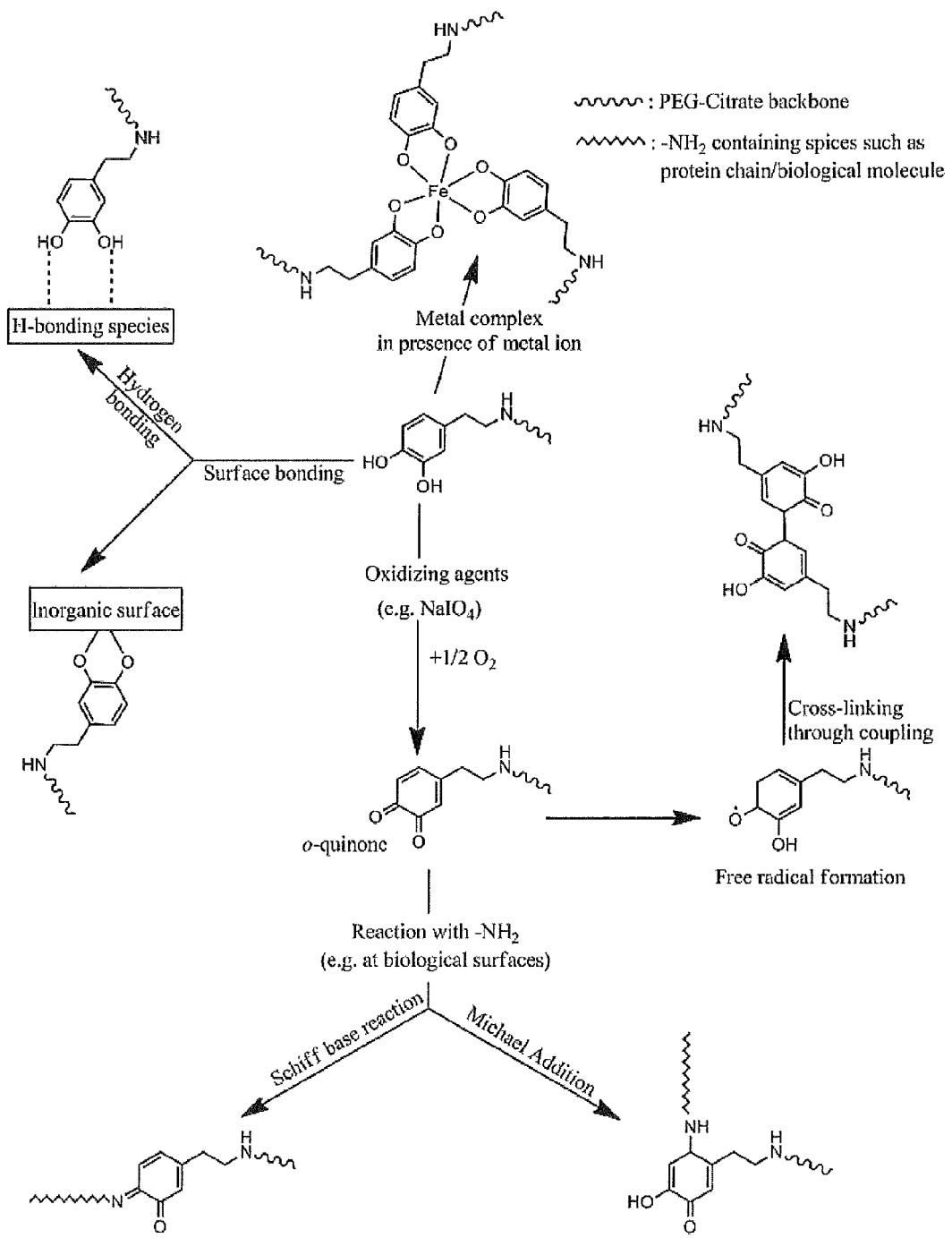
FIG. 2 illustrates a scheme of various crosslinking and surface bonding mechanisms of a polymer or oligomer or crosslinked polymer network according to some embodiments described herein.

A polymer or oligomer can be crosslinked to form a crosslinked polymer network in any manner not inconsistent with the objectives of the present invention. In some embodiments, for example, a polymer or oligomer is crosslinked with a multivalent metal ion, such as a transition metal ion. In some cases, a multivalent metal ion used as a crosslinker of the polymer or oligomer comprises one or more of Fe, Ni, Cu, Zn, or Al, including in the +2 or +3 state. In some embodiments, a polymer or oligomer is crosslinked through a functional group of a monomer or reactant described herein, such as through a functional group of an unsaturated alcohol and/or a functional group of a catechol-containing species. In some embodiments, a polymer or oligomer is crosslinked through a catechol moiety, including an oxidized catechol moiety or a catechol moiety comprising a free radical. An oxidized catechol moiety, in some embodiments, comprises an o-quinone moiety. In some embodiments, a polymer or oligomer is crosslinked through a plurality of free-radical-coupled catechol moieties, as shown, for instance, in FIG. 2. In some embodiments, a polymer or oligomer is crosslinked through one or more carbon-carbon double bonds of an unsaturated alcohol described herein. FIG. 2 illustrates a scheme of crosslinking reactions of a polymer or oligomer described herein, including through a catechol moiety of the polymer or oligomer.

Other crosslinking reactions can also be used. For example, in some embodiments, a polymer or oligomer is crosslinked through the reaction of a catechol moiety with a crosslinker comprising an —NH$_2$, —SH, —OH, or —COOH moiety or a combination thereof. In some embodiments, a crosslinker comprises a plurality of —NH$_2$, —SH, —OH, and/or —COOH moieties. For instance, in some embodiments, a polymer or oligomer is crosslinked through the reaction of a catechol moiety with a diamine-, dithiol-, diol-, and/or dicarboxylic-containing chemical species. Such a species, in some embodiments, can be a polymer or oligomer or a non-polymer or non-oligomer. In some embodiments, a polymer or oligomer is crosslinked through the reaction of a catechol moiety with a polylysine.

FIG. 2 also illustrates a scheme of surface bonding and other coupling reactions of a polymer or oligomer or crosslinked polymer network described herein, including through a catechol moiety of the polymer or oligomer or crosslinked polymer network. As illustrated in FIG. 2, in some embodiments, a polymer or oligomer or crosslinked polymer network described herein can be bonded to a surface. The surface, in some embodiments, is a surface of an inorganic material such as a mineral or oxide material. In other embodiments, the surface is a surface of an organic material or biological tissue, including bone tissue or teeth. A polymer or oligomer or crosslinked polymer network can be bonded to a surface in any manner not inconsistent with the objectives of the present invention. In some embodiments, for instance, a polymer or oligomer or crosslinked polymer network is bonded to a surface through one or more covalent bonds. In some embodiments, a polymer or oligomer or crosslinked polymer network is bonded to a surface through one or more non-covalent bonds, such as one or more ionic bonds or one or more electrostatic interactions or hydrogen bonds. Further, in some embodiments, a polymer or oligomer or crosslinked polymer network is bonded to a surface through a functional group of a monomer or reactant described herein, such as through a functional group of a catechol-containing species. In some embodiments, a polymer or oligomer or crosslinked polymer network is bonded to a surface through a catechol moiety, including an oxidized catechol moiety such as an o-quinone moiety. In some embodiments, a polymer or oligomer or crosslinked polymer network is bonded to a surface through a chemical linkage formed by a Schiff base reaction or a Michael addition of a moiety of the polymer or oligomer or crosslinked network with a moiety on the surface, such as a —NH$_2$, —SH, —OH, or —COOH moiety on a biological surface, for example.

In addition, in some embodiments, a composition described herein further comprises a particulate material mixed with a polymer or oligomer. In some embodiments, a particulate material is dispersed in a polymer network formed by a crosslinked polymer or oligomer described herein. In some embodiments, a particulate material is partially or fully encapsulated or entrapped in the polymer network. Thus, in some embodiments, a composition described herein comprises a composite of particulate material and polymer or oligomer or crosslinked polymer network.

Any particulate material not inconsistent with the objectives of the present invention may be used. In some embodiments, a particulate material comprises one or more of hydroxyapatite, tricalcium phosphate, biphasic calcium phosphate, bioglass, ceramic, magnesium powder, magnesium alloy, and decellularized bone tissue particles. In addition, a particulate material described herein can be present in a composite in any amount not inconsistent with the objectives of the present invention. In some embodiments, for instance, a composite comprises up to about 50 weight percent, up to about 70 weight percent, or up to about 99 weight percent of a particulate material, based on the total dry weight of the particulate material plus the polymer or oligomer (or the crosslinked polymer network if the polymer or oligomer is crosslinked). In some embodiments, a composite comprises between about 1 weight percent and about 99 weight percent, between about 10 weight percent and about 70 weight percent, or between about 30 weight percent and about 50 weight percent particulate material. For example, in some embodiments, a composite comprises up to about 70 weight percent hydroxyapatite.

Moreover, in some embodiments, a composition described herein further comprises bone tissue or dental tissue adhered to a composite of particulate material and polymer or oligomer (or crosslinked polymer network) described herein. Any bone or dental tissue not inconsistent with the objectives of the present invention may be adhered to a composite described herein. For example, in some embodiments, bone tissue comprises osteoblast cells or a precursor of an osteoblast cell.

In addition, in some embodiments, a composition described herein further comprises a drug mixed with a polymer or oligomer or crosslinked polymer network. In some embodiments, the drug is dispersed in a polymer network formed by a crosslinked polymer or oligomer described herein. In some embodiments, the drug is partially or fully encapsulated or entrapped in the polymer network. In some embodiments, a drug described herein is chemically bonded to a polymer or oligomer or crosslinked polymer network described herein, such as through one or more covalent bonds. One or more covalent bonds, in some embodiments, comprise bonds between a hydroxyl or carboxyl group of the polymer or oligomer or crosslinked polymer network and an appropriate functional group on the drug, such as an amine group or hydroxyl group. In some embodiments, a drug is chemically bonded to a polymer or oligomer or crosslinked polymer network through one or more ionic bonds, electrostatic bonds, or hydrogen bonds.

Thus, in some embodiments, a composition described herein comprises a drug-loaded composite of a drug and a polymer or oligomer or crosslinked polymer network. Moreover, in some embodiments, a drug is reversibly encapsulated in or bonded to the composite. In some embodiments, a drug can be released from the composite by diffusion over time or in response to a change in external environment, such as a change in pH. In some embodiments, a drug is mixed with a polymer or oligomer or crosslinked polymer network having a plurality of pendant —COOH groups. Such a polymer or oligomer or crosslinked polymer network, in some embodiments, can be a pH-sensitive polymer or oligomer or crosslinked polymer network. A pH-sensitive polymer or oligomer or crosslinked polymer network, in some embodiments, can release an encapsulated drug or a portion of an encapsulated drug in a pH-dependent manner. Therefore, in some embodiments, a composition described herein can be used a pH-triggered drug delivery vehicle.

Any drug not inconsistent with the objectives of the present invention may be used. In some embodiments, for example, a drug comprises an anti-cancer drug. In some embodiments, a drug comprises a prostaglandin antagonist. In some embodiments, a drug comprises a proton-pump inhibitor. In some embodiments, a drug comprises a hemostatic composition or an anti-hemorrhage composition. In some embodiments, a drug comprises doxorubicin (DOX). Moreover, a drug described herein, in some embodiments, is water soluble. In other embodiments, a drug is disposed in a polymeric micelle.

A drug described herein can be present in a composition in any amount not inconsistent with the objectives of the present invention. In some embodiments, for instance, a drug-loaded composite comprises up to about 5 weight percent, up to about 10 weight percent, or up to about 30 weight percent of a drug, based on the total weight of the drug plus the dry polymer or oligomer or crosslinked polymer network of the composite. In some embodiments, a composite comprises between about 0.1 weight percent and about 30 weight percent, between about 0.1 weight percent and about 10 weight percent, or between about 0.1 weight percent and about 5 weight percent drug.

Further, in some embodiments, a polymer or oligomer or crosslinked polymer network described herein can be in nanoparticulate form. Nanoparticles of a polymer or oligomer or crosslinked polymer network described herein, in some embodiments, have a size in at least one dimension between about 100 nm and about 1000 nm. In some embodiments, nanoparticles have a size in at least two dimensions between about 100 nm and about 1000 nm or a size in three dimensions between about 100 nm and about 1000 nm. In some embodiments, nanoparticles have a size in three dimensions between about 100 nm and about 500 nm or between about 200 nm and about 400 nm.

In addition, a polymer or oligomer or crosslinked polymer network of a composition described herein can have various properties, which in some embodiments, may provide one or more advantages in various applications, including various biological applications. For example, in some embodiments, a composition described herein exhibits injectability and/or high adhesion strength. Injectability, in some embodiments, is a function of viscosity. In some embodiments, a crosslinked polymer network described herein exhibits a gel time or set time at 25° C. of between about 10 seconds and about 500 seconds when measured according to ASTM D4473 as described hereinbelow in the Examples. Thus, in some embodiments, a composition described herein can be injectable for a time period suitable for use in some biological applications, including surgical or therapeutic applications.

In addition, in some embodiments, a crosslinked polymer network described herein can exhibit a glass transition temperature ($T_g$) below room temperature, when measured by differential scanning calorimetry (DSC). In some embodiments, for instance, a crosslinked polymer network described herein has a glass transition temperature between about 0° C. and about −80° C., between about 0° C. and about −60° C., or between about −5° C. and about −50° C.

Further, in some embodiments, a crosslinked polymer network described herein can exhibit various desirable mechanical properties. For instance, in some embodiments, a crosslinked polymer network exhibits a tensile strength of between about 50 kPa and about 10,000 kPa, a modulus of between about 0.05 MPa and about 50 MPa; and/or an elongation at break between about 20% and about 2000%, when measured according to ASTM D412A as described hereinbelow. In some embodiments, the tensile strength is between about 1000 kPa and about 10,000 kPa or between about 3000 kPa and about 9000 kPa. In some embodiments, the modulus is between about 0.5 MPa and about 50 MPa or between about 1 MPa and about 30 MPa. Further, the mechanical properties of a crosslinked polymer network described herein, in some embodiments, differ between the dry and swollen states of the polymer network, as described further hereinbelow.

In addition, in some embodiments, a crosslinked polymer network described herein exhibits an adhesion strength or lap shear strength of between about 20 kPa and about 150 kPa, between about 20 kPa and about 100 kPa, or between about 30 kPa and about 130 kPa, when measured according to ASTM D1002-05 as described hereinbelow. Therefore, in some embodiments, a composition described herein can be used as an adhesive, including a bioadhesive.

Further, in some embodiments, a crosslinked polymer network described herein exhibits a sol content of less than about 40%, less than about 20%, less than about 10%, or less than about 5% when determined as described hereinbelow. In some embodiments, the sol content is between about 1% and about 35% or between about 1% and about 15%.

In some embodiments, a crosslinked polymer network described herein has a swelling ratio of up to about 5000%, up to about 4000%, up to about 2000%, or up to about 1000% when determined as described hereinbelow. In some embodiments, the swelling ratio is between about 100% and about 5000% or between about 400% and about 4000%.

In addition, in some embodiments, a crosslinked polymer network described herein is biodegradable. A biodegradable polymer network, in some embodiments, degrades in vivo to non-toxic components which can be cleared from the body by ordinary biological processes. In some embodiments, a biodegradable polymer network described herein completely or substantially completely degrades in vivo over the course of about 30 days or less, when measured as described hereinbelow in Example 2 (where complete degradation corresponds to 100% mass loss). Moreover, in some embodiments, a polymer network described herein is biocompatible or cytocompatible. A biocompatible or cytocompatible polymer network, in some embodiments, is non-toxic and does not cause substantial tissue inflammation.

Moreover, the various properties of a polymer or oligomer or crosslinked polymer network described herein can be modified by altering the identities and/or amounts of the various components of the composition, including the identities and/or amounts of one or more of the following: the species used to form a polymer or oligomer, the materials mixed with or encapsulated in a polymer or oligomer or crosslinked polymer network, and the degree of crosslinking of a polymer or oligomer or crosslinked polymer network.

II. Methods of Making a Composition

In another aspect, methods of making a composition are described herein. In some embodiments, a method of making a composition comprises providing a polycarboxylic acid; providing an alcohol; combining the polycarboxylic acid with the alcohol; adding a catechol-containing species to the combination of the polycarboxylic acid and the alcohol; and forming a polymer or oligomer from the polycarboxylic acid, the alcohol, and the catechol-containing species. In some embodiments, combining the polycarboxylic acid with the alcohol comprises forming an ester bond between the polycarboxylic acid and the alcohol.

Further, in some embodiments, a method described herein is carried out in a single step and/or in a single reaction vessel. For example, in some embodiments, a polymer or oligomer formed by a method described herein comprises a random or statistical polymer or oligomer formed from the polycarboxylic acid, alcohol, and catechol-containing species. A random or statistical polymer or oligomer, in some embodiments, is formed by a polycondensation reaction, such as that illustrated in FIG. 1. In other embodiments, a polymer or oligomer backbone is first formed by combining the polycarboxylic acid and the alcohol, followed by subsequent addition of the catechol-containing species to the polymer or oligomer backbone. In some embodiments, adding the catechol-containing species to the polymer or oligomer backbone comprises esterifying or amidifying the polymer or olgiomer backbone with the catechol-containing species through an esterification or amidation reaction.

In addition, any polycarboxylic acid, alcohol, and catechol-containing species not inconsistent with the objectives of the invention may be used in a method described herein, including any polycarboxylic acid, alcohol, and catechol-containing species described in Section I hereinabove. Thus, in some embodiments, a method described herein can be used to form a composition comprising any polymer or oligomer described in Section I hereinabove, including a polymer or oligomer of Formula (I).

For example, in some embodiments, a polycarboxylic acid comprises a chemical species of Formula (A) in Section I hereinabove. In some embodiments, a polycarboxylic acid comprises citric acid. Similarly, in some embodiments, an alcohol comprises a chemical species of Formula (B) or (B') in Section I hereinabove. In some embodiments, an alcohol comprises an alkane diol or a poly(ethylene glycol). In some embodiments, a catechol-containing species comprises a chemical species of Formula (C) in Section I hereinabove. Further, in some embodiments, a catechol-containing species comprises an amine moiety, a carboxylic acid moiety, or a hydroxyl moiety that is not part of the catechol group. In some embodiments, a catechol-containing species comprises dopamine, L-DOPA, D-DOPA, or 3,4-dihydroxyhydrocinnamic acid.

Moreover, it should be noted that the various chemical species used to form a polymer or oligomer described herein can be used in any combination and in any amounts or ratios not inconsistent with the objectives of the present invention. Further, in some embodiments, the identities, amounts, and/or ratios of the components of the polymer or oligomer can be selected based on a desired property of the polymer or oligomer, such as a desired solubility, biodegradability, molecular weight, catechol content, carboxylic acid content, or charge.

In addition, in some embodiments, a method described herein further comprises crosslinking the polymer or oligomer to form a polymer network. A polymer network, in some embodiments, comprises a hydrogel. Crosslinking a polymer or oligomer to form a polymer network can be carried out in any manner not inconsistent with the objectives of the present invention. In some embodiments, for example, crosslinking comprises adding a crosslinking initiator to the polymer or oligomer. Any crosslinking initiator not inconsistent with the objectives of the present invention may be used. For instance, in some embodiments, a crosslinking initiator comprises an oxidizing agent, including an oxidizing agent that can oxidize a catechol moiety to an o-quinone. In some embodiments, an oxidizing agent comprises one or more of sodium periodate, hydrogen peroxide, tyrosinase, silver nitrate, and horseradish peroxidase. Other oxidizing agents may also be used. In some embodiments, a crosslinking initiator comprises a multivalent metal ion, including a multivalent metal ion described in Section I hereinabove.

Any amount of crosslinking initiator not inconsistent with the objectives of the present invention may be used. In some embodiments, the amount of crosslinking initiator is up to about 20 weight percent, based on the weight of the initiator (as the numerator) compared to the weight of the dry polymer or oligomer (as the denominator). In some embodiments, the amount of crosslinking initiator is between about 1 weight percent and about 20 weight percent, between about 1 weight percent and about 15 weight percent, between about 1 weight percent and about 10 weight percent, or between about 2 weight percent and about 8 weight percent. Moreover, in some embodiments, the amount of crosslinking initiator is selected based on a desired gel time, a desired degree of crosslinking, and/or a desired adhesion strength of a crosslinked polymer network.

Further, in some embodiments, a polymer or oligomer is crosslinked through a functional group of a chemical species or reactant described herein, such as through a functional group of an unsaturated alcohol and/or a functional group of a catechol-containing species. In some embodiments, a polymer or oligomer is crosslinked through a catechol moiety, including an oxidized catechol moiety or a catechol moiety comprising a free radical. An oxidized catechol moiety, in some embodiments, comprises an o-quinone moiety. In some embodiments, a polymer or oligomer is crosslinked through a plurality of free-radical-coupled catechol moieties, as shown, for instance, in FIG. 2. In some embodiments, a polymer or oligomer is crosslinked through one or more carbon-carbon double bonds of an unsaturated alcohol described herein.

Moreover, in some embodiments, a polymer or oligomer is crosslinked through the reaction of a catechol moiety with a crosslinker comprising an —$NH_2$, —SH, —OH, or —COOH moiety or a combination thereof. In some embodiments, a crosslinker comprises a plurality of —$NH_2$, —SH, —OH, and/or —COOH moieties. For instance, in some embodiments, a polymer or oligomer is crosslinked through the reaction of a catechol moiety with a diamine-, dithiol-, diol-, and/or dicarboxylic-containing chemical species. Such a species, in some embodiments, can be a polymer or oligomer or a non-polymer or non-oligomer. In some embodiments, a polymer or oligomer is crosslinked through the reaction of a catechol moiety with a polylysine.

Additionally, as illustrated in FIG. 2, a method described herein, in some embodiments, further comprises bonding a polymer or oligomer or crosslinked polymer network to a surface. The surface, in some embodiments, is a surface of an inorganic material such as a mineral or oxide material. In other embodiments, the surface is a surface of an organic material or a biological tissue, including bone tissue or teeth. Further, surface bonding can be carried out in any manner not inconsistent with the objectives of the present invention, including in any manner described in Section I hereinabove. In some embodiments, for instance, a polymer or oligomer or crosslinked polymer network is bonded to a surface through one or more covalent bonds. In some embodiments, a polymer or oligomer or crosslinked polymer network is bonded to a surface through one or more non-covalent bonds, such as one or more ionic bonds or one or more electrostatic interactions or hydrogen bonds. Further, in some embodiments, a polymer or oligomer or crosslinked polymer network is bonded to a surface through a functional group of a chemical species or reactant described herein, such as through a functional group of a catechol-containing chemical species. In some embodiments, a polymer or oligomer or crosslinked polymer network is bonded to a surface through a catechol moiety, including an oxidized catechol moiety such as an o-quinone moiety. In some embodiments, a polymer or oligomer or crosslinked polymer network is bonded to a surface through a chemical linkage formed by a Schiff base reaction or a Michael addition of a moiety of the polymer or oligomer or crosslinked network with a moiety on the surface, such as a —$NH_2$, —SH, —OH, or —COOH moiety on a biological surface.

Moreover, in some embodiments, a method described herein further comprises forming nanoparticles of a polymer network. In some embodiments, nanoparticles are formed by crosslinking a polymer or oligomer described herein in solution under sonication. In some embodiments, forming nanoparticles of a polymer network further comprises filtering the solution following crosslinking and sonication. Nanoparticles of a polymer network formed in this manner, in some embodiments, have a size in at least one dimension between about 100 nm and about 1000 nm. In some embodiments, nanoparticles have a size in at least two dimensions between about 100 nm and about 1000 nm or a size in three dimensions between about 100 nm and about 1000 nm. In some embodiments, nanoparticles have a size in three dimensions between about 100 nm and about 500 nm or between about 200 nm and about 400 nm.

Additionally, in some embodiments, a method described herein further comprises adding a particulate material to a polymer or oligomer or a crosslinked polymer network. In some embodiments, adding a particulate material comprises encapsulating or entrapping the particulate material (fully or partially) in a polymer network. Further, in some embodiments, a particulate material is added to a polymer or oligomer prior to crosslinking the polymer or oligomer. Any particulate material not inconsistent with the objectives of the present invention may be used, including any particulate material described in Section I hereinabove. For example, in some embodiments, a particulate material comprises one or more of hydroxyapatite, tricalcium phosphate, biphasic calcium phosphate, bioglass, ceramic, magnesium powder, magnesium alloy, and decellularized bone tissue particles. Moreover, a particulate material can be added in any amount not inconsistent with the objectives of the present invention. In some embodiments, for instance, up to about 50 weight percent, up to about 70 weight percent, or up to about 99 weight percent of a particulate material is added, based on the total dry weight of the particulate material plus the polymer or oligomer or crosslinked polymer network formed by the method. In some embodiments, between about 1 weight percent and about 99 weight percent, between about 10 weight percent and about 70 weight percent, or between about 30 weight percent and about 50 weight percent particulate material is used.

In some embodiments, a method described herein further comprises adding a drug to a polymer or oligomer or crosslinked polymer network. In some embodiments, adding a drug comprises encapsulating or entrapping the particulate drug (fully or partially) in a polymer network. Further, in some embodiments, a drug is added to a polymer or oligomer prior to crosslinking the polymer or oligomer. In other embodiments, a drug is added to a previously crosslinked polymer network, including a crosslinked polymer network in nanoparticulate form. Any drug not inconsistent with the objectives of the present invention may be used, including any drug described in Section I hereinabove. For example, in some embodiments, a drug comprises an anti-cancer drug or a hemostatic drug. Moreover, a drug can be added in any amount not inconsistent with the objectives of the present invention. In some embodiments, for instance, up to about 5 weight percent, up to about 10 weight percent, or up to about 30 weight percent of a drug is added, based on the total weight of the drug plus the dry polymer or oligomer or crosslinked polymer network formed by the method. In some embodiments, between about 0.1 weight percent and about 30 weight percent, between about 0.1 weight percent and about 10 weight percent, or between about 0.1 weight percent and about 5 weight percent drug is used.

III. Applications of Compositions

In another aspect, various applications of compositions are described herein. Compositions described herein, in some embodiments, can be used for various applications, including various biological applications. In some embodiments, for example, a composition described herein can be used as a bioadhesive. Thus, in some embodiments, methods of adhering biological tissue are described herein.

In some embodiments, a method of adhering biological tissue comprises disposing a composition described herein between a first portion of biological tissue and a second portion of biological tissue. The composition can comprise any composition described hereinabove in Section I. In addition, the composition can be disposed between the first and second portions of biological tissue in any manner not inconsistent with the objectives of the present invention. In some embodiments, for example, disposing a composition comprises injecting a composition. In addition, in some embodiments, a crosslinking initiator described herein is also injected at the same time as a composition described herein.

Moreover, the first and second portions of biological tissue can comprise any biological tissue not inconsistent with the objectives of the present invention. In some embodiments, for instance, a first and/or second portion of biological tissue comprises bone tissue or dental tissue. In other embodiments, a first and/or second portion of biological tissue comprises soft tissue such as skin tissue. Additionally, in some embodiments, a method of adhering biological tissue described herein further comprises contacting the first portion of biological tissue with the second portion of biological tissue. In some embodiments, contacting the first and second portions of biological tissue comprises closing a wound. Further, contacting the first and second portions of biological tissue can be carried out in any manner not inconsistent with the objectives of the present invention. In some embodiments, contacting first and second portions of biological tissue comprises suturing or stapling the portions. In other embodiments of methods described herein, the portions are contacted without the use of sutures or staples.

In some embodiments, a composition described herein can also be used to treat disease or infection. Therefore, in some embodiments, methods of treating disease are described herein. In some embodiments, a method of treating disease comprises disposing a composition described herein in a biological compartment. Any composition described in Section I hereinabove may be used. For example, in some embodiments, the composition comprises a drug. Moreover, a composition may be disposed in any biological compartment in any manner not inconsistent with the objectives of the present invention. In some embodiments, for instance, a composition is injected into a biological compartment. A biological compartment, in some embodiments, comprises a wound site, including a flesh wound site or a broken bone site.

In addition, in some embodiments of methods of treating disease described herein, a composition comprises a drug and the method further comprises releasing the drug of the composition into the biological compartment. In some embodiments, releasing a drug comprises allowing the drug to diffuse out of the composition, such as out of a crosslinked polymer network described herein. In some embodiments, releasing a drug comprises providing an external stimulus such as a change in pH of the environment of a crosslinked polymer network. Thus, in some embodiments, a composition described herein can be used to treat a variety of diseases or infections, depending on the drug used. For example, a disease can comprise cancer when an anti-cancer drug is used, or a disease can comprise a bleeding or hemorrhaging condition when a hemostatic or anti-hemorrhaging drug composition is used.

In some embodiments, a composition described herein can also be used in bioengineering applications, including tissue scaffold applications. Thus, in some embodiments, methods of promoting biological tissue growth are described herein. In some embodiments, a method of promoting biological tissue growth comprises providing a scaffold comprising a composition described herein and disposing the scaffold in a tissue growth medium. Any composition described in Section I hereinabove may be used. For example, in some embodiments, a composition comprises a particulate material described herein, including hydroxyapatite. Additionally, a scaffold can be disposed in any tissue growth medium not inconsistent with the objectives of the present invention. In some embodiments, for instance, a scaffold is disposed in an in vitro tissue growth medium, such as a cell culture plate and/or culture medium described hereinbelow in the Examples. In other embodiments, a scaffold is disposed in an in vivo tissue growth medium, such as a biological compartment described herein.

Some embodiments described herein are further illustrated in the following non-limiting examples. All chemicals, cell culture media, and supplements described in the following examples were purchased from Sigma Aldrich (St. Louis, Mo.), except where mentioned otherwise. All chemicals were used as received. Where relevant, quantitative data is presented as mean±standard deviation, with a sample number of at least 5. The significance of differences between results was evaluated by a one-way ANOVA test. In some tests, p<0.05 (*) was considered statistically significant, and in some other tests p<0.01(**) was considered to be statistically significant.

EXAMPLE 1

Polymers or Oligomers

Polymers or oligomers suitable for use in compositions according to some embodiments described herein were prepared as follows. A series of polymers or oligomers were prepared using a polycondensation reaction, as illustrated in FIG. 1. Specifically, citric acid (CA) and poly(ethylene glycol) (PEG) were placed in a 250 mL three-necked round-bottom flask and heated to 160° C. using an oil bath until a molten clear mixture was formed under stirring. Next, under nitrogen gas flow, a calculated amount of dopamine or L-DOPA was added to the mixture. After allowing enough time for a clear solution to form, the temperature was reduced to 140° C. and the reaction was continued under vacuum until a desired molecular weight was obtained. The resulting polymer or oligomer was dissolved in deionized (DI) water and purified by dialysis using a 500- or 1000-MWCO (molecular weight cut-off) dialysis tube. The MWCO was chosen based on the molecular weight of the PEG used in the synthesis. The dialyzed solution was then lyophilized to obtain the pure polymer or oligomer. Different polymers or oligomers were synthesized using different PEG lengths and various amounts of dopamine, as shown in Table 1. In the nomenclature used in Table 1, a polymer or oligomer designated as iCMBA-$P_aD_b$ was formed using a PEG having a number average molecular weight (MW) of a and a molar amount of dopamine of b, relative to the amount of PEG. For example, the polymer or oligomer designated as iCMBA-$P_{400}D_{0.1}$ was formed using a PEG having a molecular weight of 400 and a molar amount of dopamine of 0.1. The "feeding ratio" in Table 1 is the ratio of the mole fractions of the three starting materials. The "composition ratio" is the measured ratio of the mole fractions of the components in the final polymer or oligomer, as described below.

TABLE 1

| Polymers or oligomers. | | | | |
|---|---|---|---|---|
| Polymer or oligomer | Mw of PEG (Da) | CA: PEG:D (moles) | CA: PEG:D Feeding Ratio | CA: PEG:D Composition Ratio |
| iCMBA-$P_{400}$ $D_{0.1}$ | 400 | 1.1:1:0.1 | 0.50:0.45:0.05 | 0.49:0.46:0.05 |
| iCMBA-$P_{400}$ $D_{0.3}$ | 400 | 1.1:1:0.3 | 0.46:0.42:0.12 | 0.46:0.43:0.11 |
| iCMBA-$P_{400}$ $D_{0.5}$ | 400 | 1.1:1:0.5 | 0.42:0.38:0.20 | 0.41:0.42:0.17 |
| iCMBA-$P_{200}$ $D_{0.3}$ | 200 | 1.1:1:0.3 | 0.46:0.42:0.12 | 0.46:0.44:0.10 |
| iCMBA-$P_{1000}$ $D_{0.3}$ | 1000 | 1.1:1:0.3 | 0.46:0.42:0.12 | 0.45:0.46:0.09 |

Figure 3:
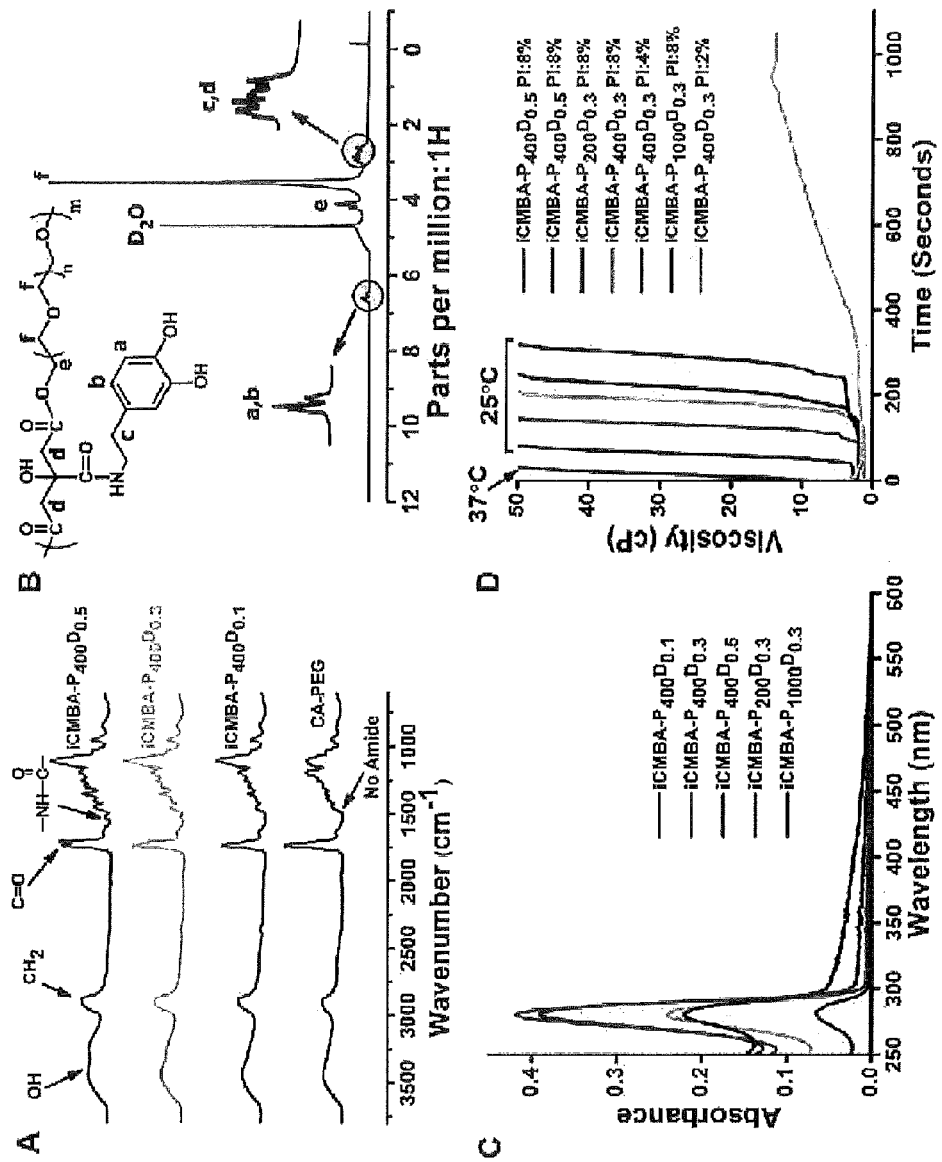
FIG. 3 illustrates spectra and viscosity measurements of polymers or oligomers and crosslinked polymer networks according to some embodiments described herein.

The polymers or oligomers prepared as described above were characterized using Fourier Transform infrared (FT-IR) spectroscopy, proton nuclear magnetic resonance ($^1$H-NMR) spectroscopy, and ultraviolet-visible (UV-vis) spectroscopy. Samples for FT-IR analysis were prepared by casting a 1% (w/v) solution of polymer or oligomer in 1,4-dioxane onto a potassium bromide crystal disc and allowing the disc to completely dry in a fume hood. The spectroscopy was then performed using a Nicolet 6700 FT-IR (Thermo Scientific, Waltham, Mass.) equipped with OMNIC software. For NMR analysis, 1% (w/v) solution of a polymer or oligomer in deuterium oxide was placed into a 5-mm (outer diameter) NMR tube and analyzed using a 250 MHz JNM ECS 300 NMR (JEOL, Tokyo, Japan). For UV-Vis analysis, the absorbance of a 0.02% (w/v) solution of a polymer or oligomer in DI water was measured using a Shimadzu UV-vis spectrophotometer from 200 nm to 700 nm. Representative spectra are illustrated in FIG. 3 (A=FT-IR, B=NMR, C=UV-Vis), along with some spectroscopic assignments. The final composition of the polymers or oligomers of Table 1 was calculated by comparing the area under the peaks of the phenyl protons with the area under the peaks of the citric acid protons and with the area under the peaks of the PEG methylene groups.

EXAMPLE 2

Crosslinked Polymer Networks

Crosslinked polymer networks according to some embodiments described herein were prepared as follows. Polymers or oligomers prepared as described in Example 1 were dissolved in DI water and then mixed with a solution of sodium meta-periodate (PI) in DI water. Crosslinking was then allowed to proceed. Not intending to be bound by theory, it is believed that PI causes oxidation of the hydroxyl groups of the catechol moiety, leading to crosslinking of catechol moieties. The amount of PI used was varied between 2% and 8% (w/w), based on the weights of PI and the polymer or oligomer.

Various properties of the crosslinked polymer networks were determined as follows. The gel or set time of a polymer network was defined as the time elapsed between mixing the initiator with the polymer or oligomer solution and the beginning of crosslinking. More specifically, the gel time was determined by a viscometry technique based on ASTM D4473, using a cone and plate Brookfield viscometer (Brookfield Engineering Labs, Inc, MA) equipped with a temperature control unit. Briefly, 1 mL of 50% (w/w) solution of polymer or oligomer in DI water was mixed with an equal volume of PI solution. To achieve various ratios of PI to polymer or oligomer, the concentration of PI in the PI solution was varied in different instances. Immediately after mixing the PI solution and the solution of polymer or oligomer, the combined mixture was transferred to the viscometer cup and the change in viscosity of the mixture was measured as a function of time, using a CP-42 spindle at a spinning speed of 12 revolutions per minute. The time elapsed from the start point until the onset of an abrupt increase in the viscosity of the mixture, determined according to ASTM D4473, was defined as the gel time or set time of the polymer network. The measurements were carried out at 25° C. for all samples except for iCMBA-$P_{400}D_{0.5}$ with 8% PI. The gel time of this sample was measured at two different temperatures, 25° C. and 37° C. The gel time of different polymer networks is shown in Table 2.

TABLE 2

Gel times.

| Polymer or oligomer | PI amount (w/w %) | Test temperature (° C.) | Measured gel time (sec) |
|---|---|---|---|
| iCMBA-$P_{400}D_{0.5}$ | 8% | 37 | 18 ± 2 |
| iCMBA-$P_{400}D_{0.5}$ | 8% | 25 | 46 ± 4 |
| iCMBA-$P_{200}D_{0.3}$ | 8% | 25 | 97 ± 3 |
| iCMBA-$P_{400}D_{0.3}$ | 8% | 25 | 163 ± 9 |
| iCMBA-$P_{400}D_{0.3}$ | 4% | 25 | 175 ± 13 |
| iCMBA-$P_{1000}D_{0.3}$ | 8% | 25 | 244 ± 11 |
| iCMBA-$P_{400}D_{0.3}$ | 2% | 25 | 313 ± 10 |

Mechanical properties of crosslinked polymer networks, including ultimate tensile strength, modulus and elongation at break, were measured by tensile mechanical testing according to ASTM D412A on an MTS Insight 2 fitted with a 10 N load cell (MTS, Eden Prairie, Minn.). Briefly, dog bone shaped samples of polymer networks (25 mm×6 mm×1.5 mm, length×width×thickness) were pulled at a rate of 500 mm/minute and elongated to failure. Measured values were converted to stress-strain curves, and the initial modulus was calculated from the initial slope of the curve (0-10% elongation). In order to evaluate the effect of hydration on the mechanical properties of crosslinked polymer networks, the mechanical tests were also conducted on the crosslinked polymer networks when they were fully swollen hydrogels. To achieve a fully swollen state, the polymer networks were swollen in water for 4 hours.

Figure 4:
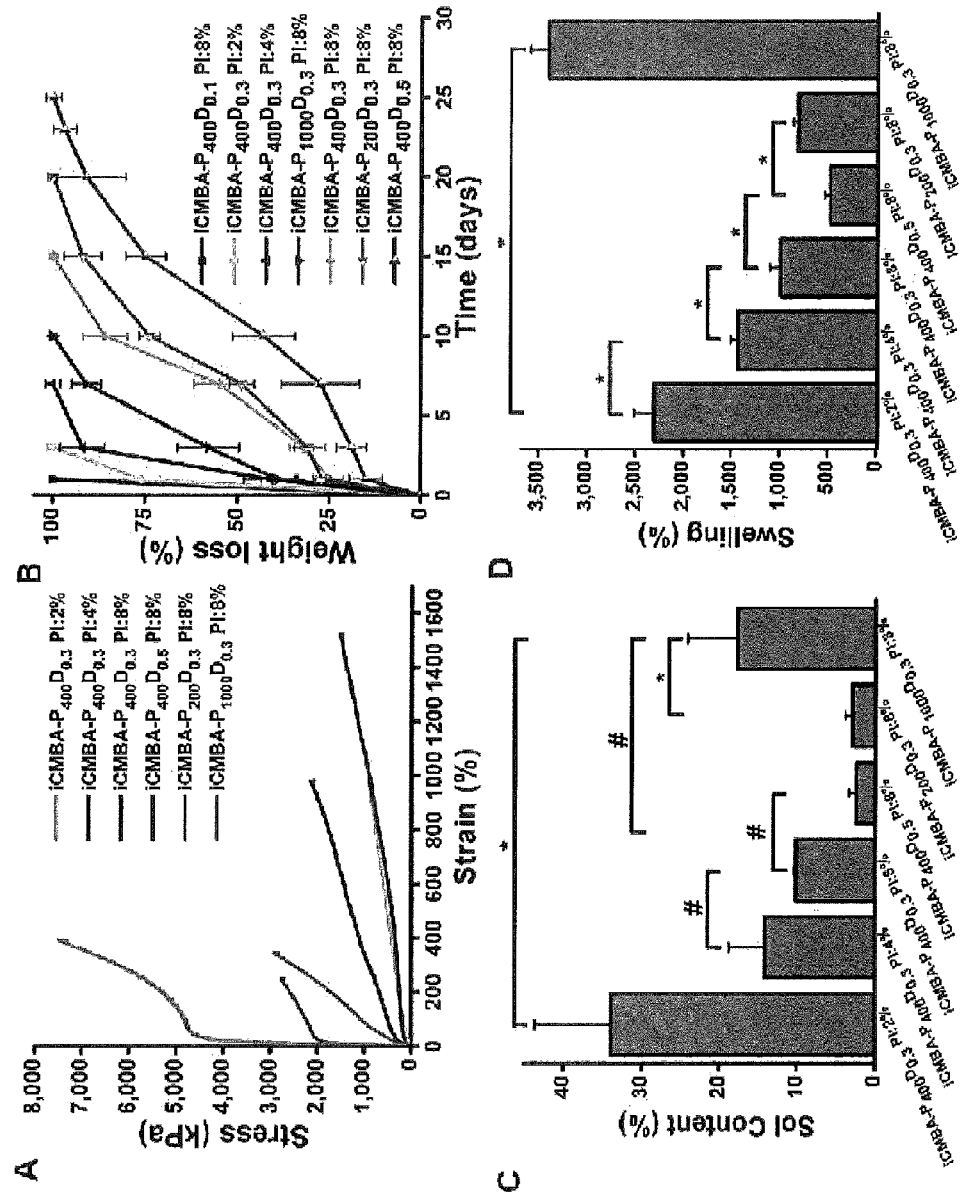
FIG. 4 illustrates some properties of crosslinked polymer networks according to some embodiments described herein.

Mechanical properties of some crosslinked polymer networks in dry and fully swollen states are listed in Table 3. The PI ratio in Table 3 is the (w/w %) of the PI to the polymer or oligomer. All crosslinked polymer networks demonstrated rubber-like (elastomeric) behavior. Stress-strain curves are illustrated in FIG. 4A.

TABLE 3

Mechanical properties.

| Polymer or oligomer | PI Ratio (w/w) | Tensile strength (kPa) | | Elongation at break (%) | | Modulus (MPa) | |
|---|---|---|---|---|---|---|---|
| | | Dry | Swollen | Dry | Swollen | Dry | Swollen |
| iCMBA-$P_{400}D_{0.3}$ | 2% | 1082.6 ± 166.4 | — | 962.2 ± 78.1 | — | 0.356 ± 0.05 | — |
| iCMBA-$P_{400}D_{0.3}$ | 4% | 1644 ± 84.3 | — | 1582.5 ± 144.6 | — | 0.73 ± 0.05 | — |
| iCMBA-$P_{400}D_{0.3}$ | 8% | 2067.3 ± 732 | 69 ± 7 | 911.8 ± 405.8 | 143.5 ± 46 | 1.61 ± 0.66 | 0.068 ± 0.007 |
| iCMBA-$P_{400}D_{0.5}$ | 8% | 2931.4 ± 514.9 | 216 ± 57.2 | 296.1 ± 83.9 | 41.6 ± 6 | 2.61 ± 0.57 | 0.69 ± 0.14 |
| iCMBA-$P_{200}D_{0.3}$ | 8% | 8515.1 ± 1167 | 242.4 ± 52.3 | 397.4 ± 26.4 | 210 ± 97.2 | 35.7 ± 6.7 | 0.202 ± 0.07 |
| iCMBA-$P_{1000}D_{0.3}$ | 8% | 3496 ± 806.2 | 82.8 ± 3.6 | 201.4 ± 49 | 132 ± 32.1 | 33.4 ± 11.9 | 0.091 ± 0.005 |

After the crosslinking reaction was carried out, the sol-gel content and the swelling ratio of the crosslinked polymer network were also measured. The measured values were based on the mass differential before and after incubation of the polymer network in a solvent or water. For the sol (soluble) content measurement, cylindrical disks of polymers (5 mm diameter; 2 mm thick) were cut from unpurified crosslinked polymer network films. The disks were weighed to find the initial mass ($W_i$), and suspended in 1,4-dioxane for 48 hours. During this period, the solvent was changed every 6 hours. Next, the samples were removed from the solvent and lyophilized for 72 hours. The dried samples, absent of any non-crosslinked polymer and solvent, were weighed to find the dry mass ($W_d$). The sol-gel fraction was then calculated using equation (1):

$$Sol(\%) = \frac{W_i - W_d}{W_i} \times 100. \quad (1)$$

The sol content was used as a measure of the non-crosslinked fraction of the polymer network. For example, for a polymer network having a sol content of 2.37%, only 2.37% of the polymer network was not crosslinked. The sol contents of different crosslinked polymer networks are shown in FIG. 4C.

To measure the swelling ratio, the leached and dried samples were suspended in water for 24 hours. Next, the samples were removed from the water, blotted dry with filter paper, and weighed to obtain a swollen weight ($W_s$). The swelling percentage was calculated using equation (2):

$$Swelling(\%) = \frac{W_s - W_d}{W_d} \times 100. \quad (2)$$

The swelling ratios of different polymer networks are shown in FIG. 4D.

Degradation of the crosslinked polymer networks was also investigated. Degradation studies were conducted in PBS (pH 7.4) at 37° C. Cylindrical disk polymer network specimens (7 mm in diameter, 2 mm thick) were cut from purified crosslinked polymer network films. The purified samples were weighed ($W_0$), placed into test tubes containing 10 mL of PBS, and incubated at 37° C. for various pre-determined time periods and until complete degradation of the polymer networks. The PBS was changed every 12 hours. After incubation, the samples were thoroughly and gently washed with DI water, lyophilized for 72 hours, and weighed. The mass loss was calculated by comparing the initial mass ($W_0$) with the mass measured at the pre-determined time points ($W_t$), as shown in equation (3):

$$Massloss(\%) = \frac{W_0 - W_t}{W_0} \times 100. \quad (3)$$

Results for some polymer networks are shown in FIG. 4B.

The adhesion strengths of different crosslinked polymer networks described herein were determined by a lap shear strength test based on ASTM D1002-05. Briefly, strips (40 mm×4 mm) of porcine-derived, acellular small intestine submucosa (SIS) material (OASIS®, HealthPoint Ltd. Fort Worth, Tex.) were prepared. After mixing a polymer or oligomer solution with a determined amount of PI solution as described hereinabove, 10 µL of the mixture was spread over an area of 6 mm×4 mm on one strip, which was pre-soaked in water. A second wet strip was subsequently brought into contact with the first strip to form a contact area of 6 mm×4 mm. The adhered strips were then placed in a highly humid chamber for 2 hours. The lap shear strength of the bonded strip specimen was subsequently measured using an MTS Insight 2 fitted with a 10 N load cell and a crosshead speed of 1.3 mm/min (MTS, Eden Prairie, Minn.). The adhesion strength of fibrin glue was also tested as a control. Some results are shown in Table 4.

TABLE 4

Adhesion strength.

| Polymer or oligomer | PI Amount (w/w %) | Lap shear strength (kPa) |
|---|---|---|
| iCMBA-$P_{400}$ $D_{0.3}$ | 2% | 39.09 ± 7 |
| iCMBA-$P_{400}$ $D_{0.3}$ | 4% | 40.4 ± 2.79 |
| iCMBA-$P_{400}$ $D_{0.3}$ | 8% | 50.73 ± 2.43 |
| iCMBA-$P_{400}$ $D_{0.5}$ | 8% | 61.3 ± 10.87 |
| iCMBA-$P_{200}$ $D_{0.3}$ | 2% | 33.41 ± 8.93 |
| iCMBA-$P_{200}$ $D_{0.3}$ | 4% | 33.84 ± 5.26 |
| iCMBA-$P_{200}$ $D_{0.3}$ | 8% | 44.99 ± 5.76 |
| iCMBA-$P_{1000}$ $D_{0.3}$ | 2% | 49.34 ± 6.49 |
| iCMBA-$P_{1000}$ $D_{0.3}$ | 4% | 90.25 ± 11.25 |
| iCMBA-$P_{1000}$ $D_{0.3}$ | 8% | 123.23 ± 13.23 |
| Fibrin glue | — | 15.38 ± 2.82 |

EXAMPLE 3

In Vitro Biocompatibility

In vitro cell compatibility of polymers or oligomers and crosslinked polymer networks according to some embodiments described herein was evaluated as follows.

To quantitatively assess in vitro cytotoxicity of polymers or oligomers described herein, a methlythiazoletetrazolium (MTT) cell proliferation and viability assay was performed. First, solutions of various polymers or oligomers in Dulbecco's modified eagle's medium (DMEM), containing 10% (v/v) fetal bovine serum (FBS) and 1% (v/v) streptomycin, were prepared in 3 different concentrations: 10, 1, and 0.1 mg/mL (polymer or oligomer/medium). Next, to each well of a 96-well cell culture plate, 200 µL of solution of NIH 3T3 fibroblast cells in DMEM (at a concentration of $5 \times 10^4$ cells/mL) was added and incubated for 24 hours at 37° C., 5% $CO_2$ and 95% relative humidity. The medium of each well was then replaced by a DMEM solution of a polymer or oligomer and incubated for another 24 hours followed by MTT assay analysis according to the manufacturer's protocol. Poly(ethylene glycol) diacrylate (PEGDA, $M_n$=700) solutions with similar concentrations were used as a control as described in Gyawali et al., "Citric acid-derived in situ crosslinkable biodegradable polymers for cell delivery," *Biomaterials* 2010, 31:9092-105. The viability of the cells in the test wells were normalized to that of cells cultured in blank medium (DMEM), and the results were described as a percent of cell viability of the test sample compared to the control. Thus, a result of 100% cell viability means the cell viability of the test sample (such as a specific solution of polymer or oligomer in DMEM) was the same as that of blank medium.

Cytotoxicity of the sol content or leachable fraction of crosslinked polymer networks described herein, referred to as sol-cytotoxicity, was also assessed by incubating an equal mass of crosslinked polymer network samples in 5 mL of cell culture medium for 24 hours. Next, three different solutions were prepared for cell cultures: 1×, 10× and 100× (1× refers to a solution of leached products with no dilution; 10× and 100× refer to 10 times and 100 times dilution, respectively, of the 1× solution with additional culture medium). Fibrin glue (Tisseel, Baxter Corp.) and blank medium were used as controls. The cell culture and MTT assay were carried out as described above.

To evaluate the cytotoxicity of the degradation products of crosslinked polymer networks, equal weight samples of various formulations of crosslinked polymer networks were fully degraded in 10 mL of complete cell culture medium. The resultant solutions were then diluted to three concentrations (1×, 10× and 100×) using DMEM. These solutions were subsequently used for cell culture and subsequent MTT analysis as described above. All the above solutions were pH-neutralized and passed through a 0.2 jam filter prior to use for cell culture.

Qualitative cytotoxicity evaluation was also carried out by observing the adhesion of NIH 3T3 fibroblast cells to crosslinked polymer network films using optical microscopy. Briefly, crosslinked polymer network films were cut into disk shaped samples (5 mm diameter and 1 mm thickness) and sterilized by incubation in 70% ethanol for 3 hours followed by exposure to UV light for another 3 hours. Then, 200 μL of 3T3 fibroblast cell solution ($5 \times 10^4$ cells/mL) was then seeded onto each sample. Using an optical microscope (Nikon Eclipse Ti-U equipped with DS-Fil camera, Nikon Instruments Inc, Melville N.Y.), the proliferation and morphology of cells on the samples were observed and photographed at different time points (1, 3, and 5 days post cell culture).

Figure 5:
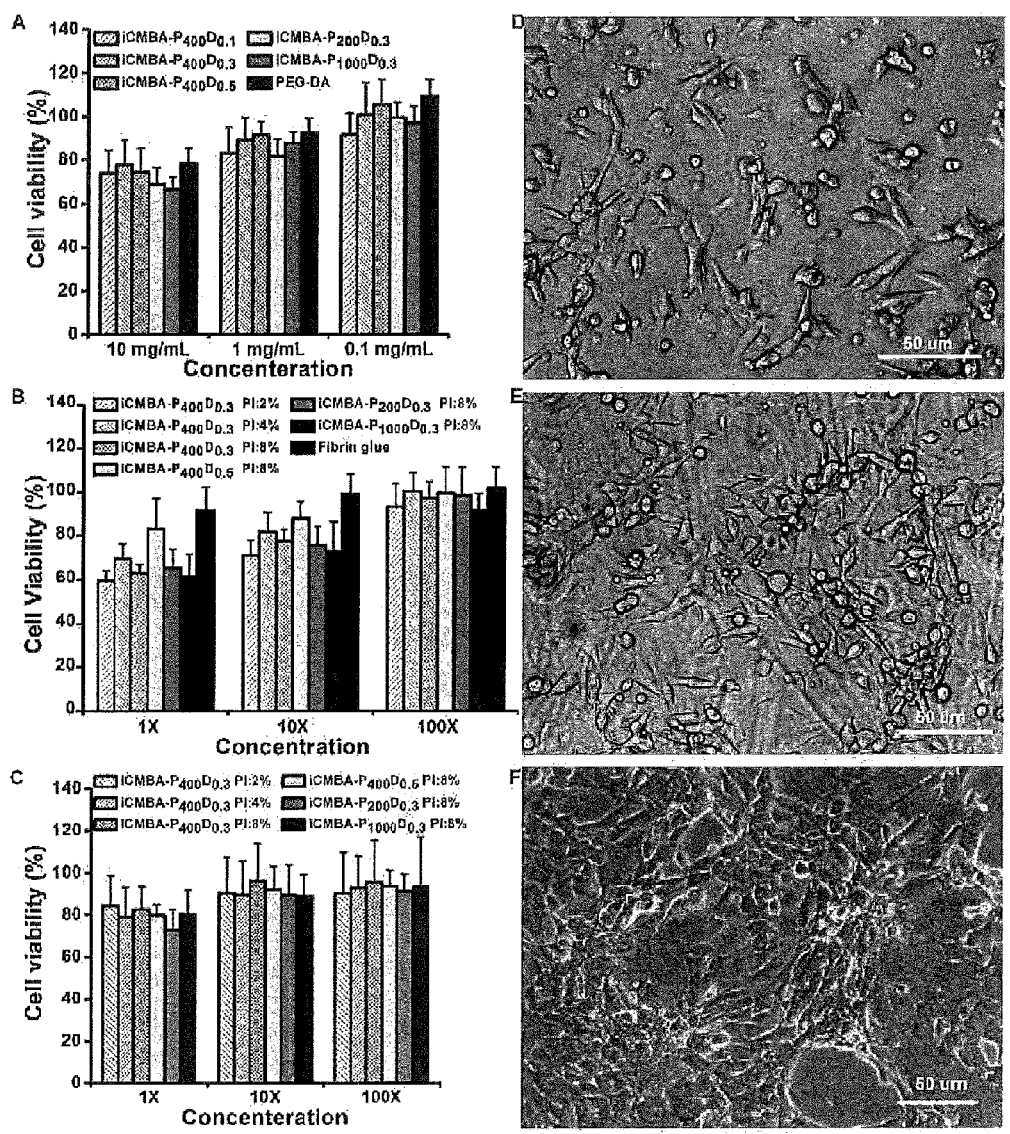
FIG. 5 illustrates the results of cytoxicity evaluations of compositions according to some embodiments described herein.

The results of the cytotoxicity evaluations are shown in FIG. 5. FIG. 5A illustrates the results for polymers or oligomers. FIG. 5B illustrates the results for the sol content or leachable fraction of crosslinked polymer networks. FIG. 5C illustrates the results for the degradation products of the crosslinked polymer networks. FIG. 5D-F illustrates the qualitative examination of NIH 3T3 fibroblast cells by light microscopy. The cells demonstrated an excellent cell attachment to the polymer films with a spindle-shape morphology. The proliferation of the cells was also observable through the increase in the number of cells throughout the three time points (FIG. 5D=1 day, E=3 days, and F=5 days post cell culture).

EXAMPLE 4

In Vivo Cell Viability and Proliferation

In vivo cell biocompatibility and wound healing properties of crosslinked polymer networks according to some embodiments described herein were evaluated as follows.

The in vivo biocompatibility and wound healing properties of the crosslinked polymer networks were evaluated using a rat skin incision model. All experiments were performed with the approval of the University of Texas at Arlington Animal Care and Use Committee (IACUC). Sprague-Dawley rats (female, average weight of 300±50 g, 5 animals/group) were sedated with an intraperitoneal injection of ketamine (40 mg/kg) and xylazine (5 mg/kg). The skin surgical area was sterilized with betadine followed by 70% ethanol. Six full-thickness wounds (2 cm long×0.5 cm deep) were made on the dorsum of each rat. Three of the wounds on each rat were closed by dropping a sterilized crosslinked polymer network according to one embodiment described herein (iCMBA-$P_{400}D_{0.5}$PI:8%) into the wounds followed by finger-clamping for about 2 minutes. The three other wounds were closed by conventional suturing as a control. To minimize variations in surgical intervention, one surgeon performed all the procedures in a uniform fashion. On the 7th and 28th days post-wounding, the test animals were sacrificed, and skin tissues at wound sites were excised for histological analyses. These sections were stained with hematoxylin and eosin (H&E) for morphological assessment. Masson trichrome staining was used to assess the collagen production. To evaluate inflammatory cells, immunohistochemistry was performed to quantify the number of CD11b positive cells using established procedures. Specifically, the tissue sections were stained with inflammatory cell marker CD11b (rabbit anti-rat Integrin αM, H-61, Santa Cruz Biotechnology), and peroxidase-conjugated goat anti-rabbit secondary antibodies (Santa Cruz Biotechnology). All histological imaging analyses were performed on a Leica microscope (Leica, Wetzlar, Germany). Cell infiltration into the incision area was quantified using Image J software by calculating cell density (number of cells per unit area) in random areas in the proximity of the incision line with the area held constant for all samples. The number of CD11b positive cells in the incision area was also determined by counting the cells in the cell infiltration area. Collagen density (as a percent) was determined using Masson trichrome staining images by calculating the ratio of blue-stained area (collagen) to total area using Image J. The healing and reconstruction of tissue in the incision area after four weeks was also evaluated by measuring the tensile strength of the regenerated tissue treated with iCMBA-$P_{400}D_{0.5}$PI:8% and comparing it with suture-closed wounds and healthy skin tissue.

It was observed that upon applying the crosslinked polymer network, the bleeding caused by creation of the wounds on the dorsum of the rats immediately stopped. In addition, the wound openings were closed within two minutes. Furthermore, the visual examination and comparison of cross-linked polymer network-treated and sutured wounds at different time points demonstrated the high efficiency of crosslinked polymer networks described herein in the wound healing process.

Figure 6:
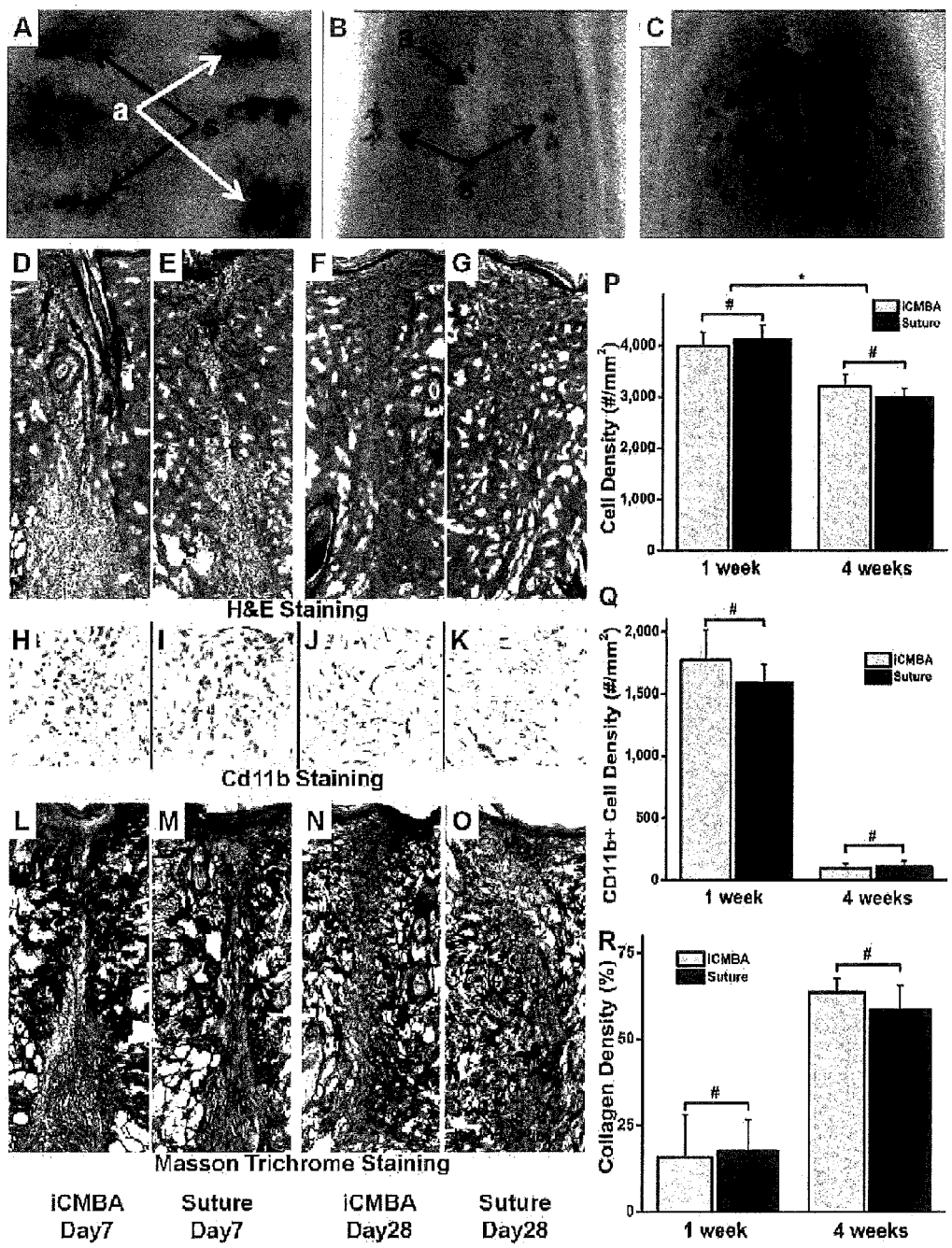
FIG. 6 illustrates in vivo evaluation results of crosslinked polymer networks according to some embodiments described herein.

FIG. 6A-C illustrates photographs of a rat's dorsum skin with created wounds that were closed by iCMBA ("a") and suture ("s") at 2 minutes (A), 7 days (B), and 28 days (C) post-wounding. FIG. 6D-O are images of H&E (hematoxylin and eosin), immunohistochemical (for CD11b), and Masson trichrome staining of sections of wounds at the 7th day post treatment with iCMBA (D, H and L) and suture (E, I, and M); and at 28th day post treatment with iCMBA (F, J, and N) and suture (G, K, and O). The original magnification was 200× for D-G and L-O, and 400× for H-K. The histological evaluation (H&E staining) at day seven showed only minor acute inflammation when the crosslinked polymer network was utilized. FIG. 6P illustrates the total cell density infiltrated into the area surrounding the incision 1 week and 4 weeks post treatment with iCMBA and suture. FIG. 6Q illustrates the number of CD11b positive cells in the vicinity of wounds treated with iCMBA and suture. FIG. 6R illustrates the collagen density in the wound area at 1-week and 4-week time points (# $p > 0.05$).

Figure 7:
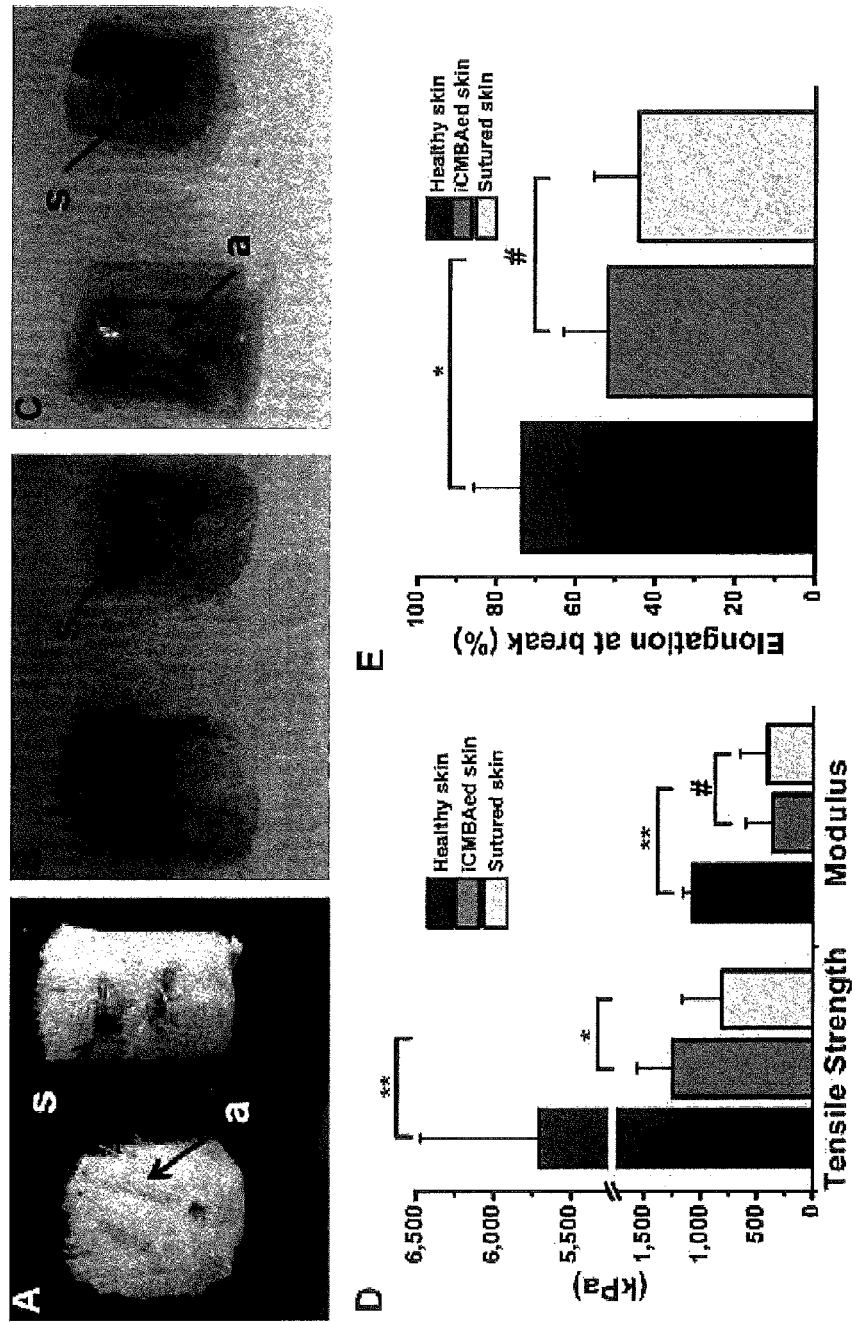
FIG. 7 illustrates in vivo evaluation results of crosslinked polymer networks according to some embodiments described herein.

In addition, as illustrated in FIG. 7, the measurement of the mechanical properties of the rat skin revealed that the skin treated with a crosslinked polymer network described herein had a higher tensile strength (1250±315 kPa) than suture-closed skin (810±355 kPa). The modulus and elongation at break were similar for both groups. The examination of the healed wounds after 28 days showed no trace of polymer at the location of healed tissue. FIGS. 7A-C are photographs of the pieces of excised skin tissue of sacrificed rats at the site of wounds treated with crosslinked polymer ("a") and suture ("s") at the 7th day (A) and 28th day (B and C, where C shows the reverse side of B) post-wounding.

EXAMPLE 5

Compositions

Figure 8:
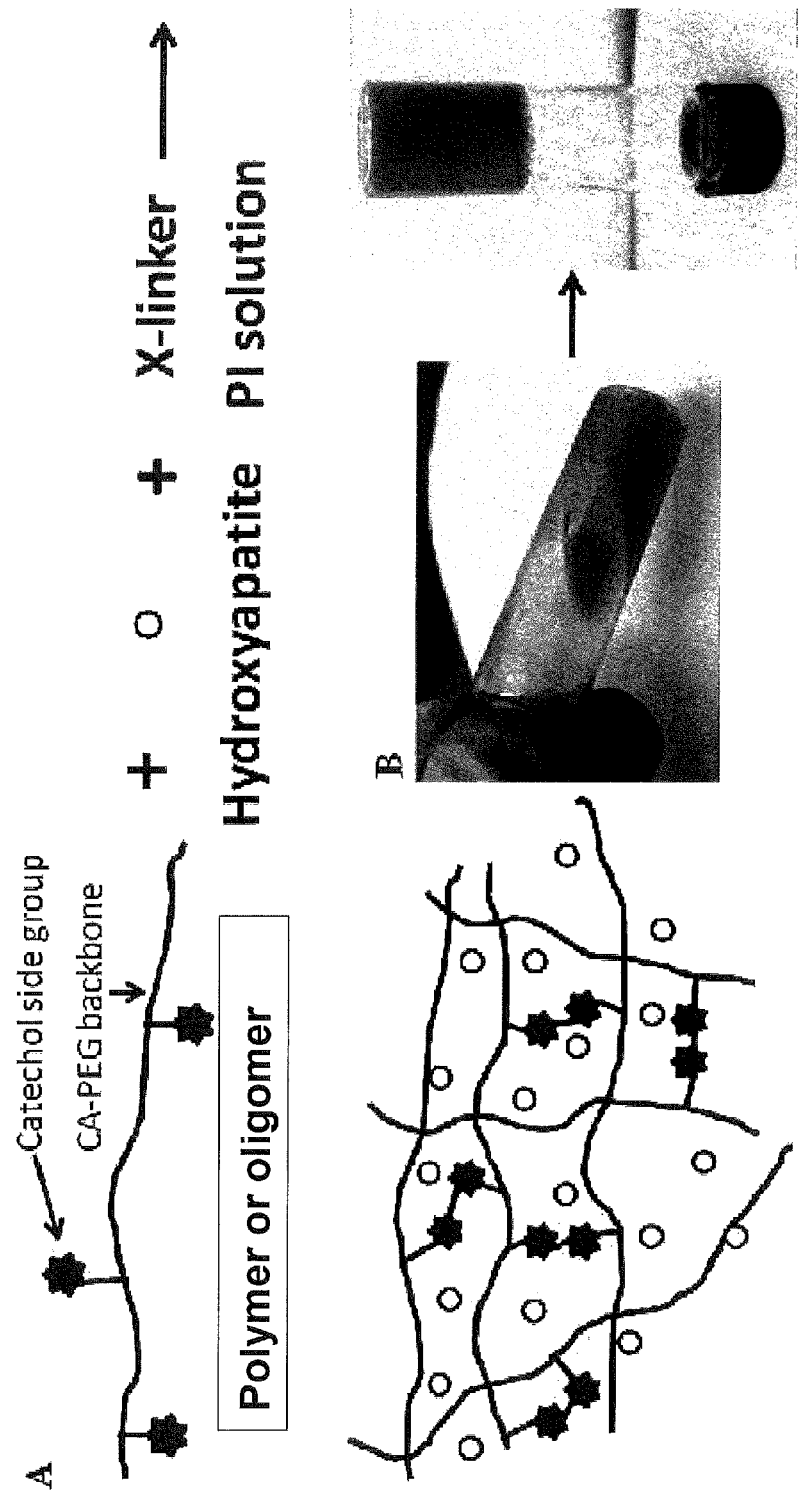
FIG. 8 illustrates a scheme of a method of making a composition according to one embodiment described herein.

Compositions according to some embodiments described herein were prepared as follows. First, a polymer or oligomer was prepared as described in Example 1. Specifically, the polymer or oligomer described as iCMBA-$P_{200}D_{0.3}$ was prepared. Next, a series of injectable composites was prepared by mixing solutions of the iCMBA in water with different amounts of hydroxyapatite (HA) to achieve various final compositions having 30, 50, and 70 wt % HA (w/w of dry composition). A calculated amount of crosslinker solution (PI in DI water) was then added to the mixture. The amount of PI was selected to provide enough time for preparation and injection of the resulting iCMBA-HA composites. In particular, the amount of PI was chosen so that the mixture maintained sufficient flowability (low viscosity) and injectability prior to completion of crosslinking. The set time of these composites was defined as the time elapsed from the addition of the PI to the iCMBA-HA mixture until the mixture was no longer flowable. The ratio of solid to liquid content was kept constant for all set time measurements. The various compositions and their set times are listed in Table 5. In the nomenclature used in Table 5, a crosslinked polymer network designated as iCMBA-$P_aD_b$-HA c % was formed using a PEG having a MW of a and a molar amount of dopamine of b, relative to the amount of PEG, and a weight percent of HA of c (w/w of HA over the total weight of the dry composite). FIG. 8A illustrates a schematic of the preparation process. FIG. 8B shows photographs of a composition before (left) and after (right) crosslinking.

TABLE 5

Compositions and Set Times.

| Composition | HA Amount (dry w/w %) | PI Amount (w/w %) | Set time (sec) |
|---|---|---|---|
| iCMBA-$P_{200}D_{0.3}$-HA30% | 30 | 4% | 247 ± 13 |
| iCMBA-$P_{200}D_{0.3}$-HA30% | 30 | 8% | 172 ± 15 |
| iCMBA-$P_{200}D_{0.3}$-HA50% | 50 | 4% | 238 ± 9 |
| iCMBA-$P_{200}D_{0.3}$-HA50% | 50 | 8% | 166 ± 11 |
| iCMBA-$P_{200}D_{0.3}$-HA70% | 70 | 4% | 231 ± 10 |
| iCMBA-$P_{200}D_{0.3}$-HA70% | 70 | 8% | 159 ± 8 |

Mechanical properties of the crosslinked HA composites were determined by unconfined compressive testing. Specifically, the measurements were conducted according to ASTM D695-10 on a MTS Insight 2 fitted with a 500 and 2000 N load cell (MTS, Eden Prairie, Minn.). Briefly, the cylindrical shaped samples (6 mm×12 mm, diameter× height) were compressed at a rate of 1.3±0.3 mm/minute and deformed to failure. Values were converted to stress-strain curves and the initial modulus was calculated from the initial slope of the curves (0-10% elongation). The mechanical tests were conducted on freshly-prepared samples (within 1 hr after preparation) as well as on samples completely dried by lyophilization. Mechanical properties of some composites are shown in Table 6.

TABLE 6

Mechanical properties.

| Composite | PI Amount (w/w %) | Compressive strength (MPa) | | Compressive modulus (MPa) | | Strain at break (%) | |
|---|---|---|---|---|---|---|---|
| | | Fresh | Dry | Fresh | Dry | Fresh | Dry |
| iCMBA-$P_{200}D_{0.3}$-HA30% | 8 | 1.25 ± 0.35 | 8.03 ± 2.30 | 1.06 ± 0.12 | 2.67 ± 0.70 | 54.08 ± 2.24 | 77.60 ± 0.9 |
| iCMBA-$P_{200}D_{0.3}$-HA50% | 8 | 1.89 ± 0.45 | 9.26 ± 2.0 | 4.31 ± 0.89 | 19.83 ± 2.1 | 52 ± 3.71 | 51.70 ± 8.0 |
| iCMBA-$P_{200}D_{0.3}$-HA70% | 8 | 2.45 ± 0.37 | 23.71 ± 2.60 | 5.74 ± 1.10 | 178.79 ± 14 | 29.46 ± 4.33 | 32.8 ± 6.06 |

Figure 9:
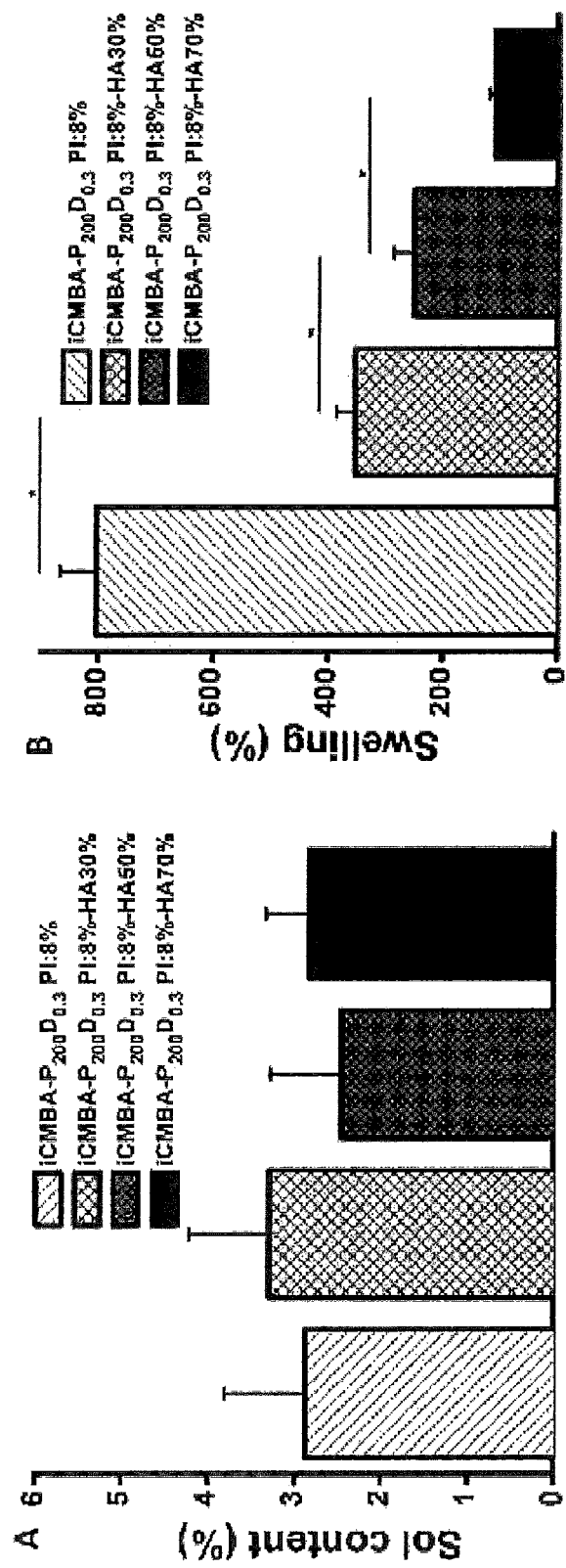
FIG. 9 illustrates some properties of composites according to some embodiments described herein.

The sol-gel content and the swelling ratio of the composites were measured as described in Example 2. The results are provided in FIG. 9.

Figure 10:
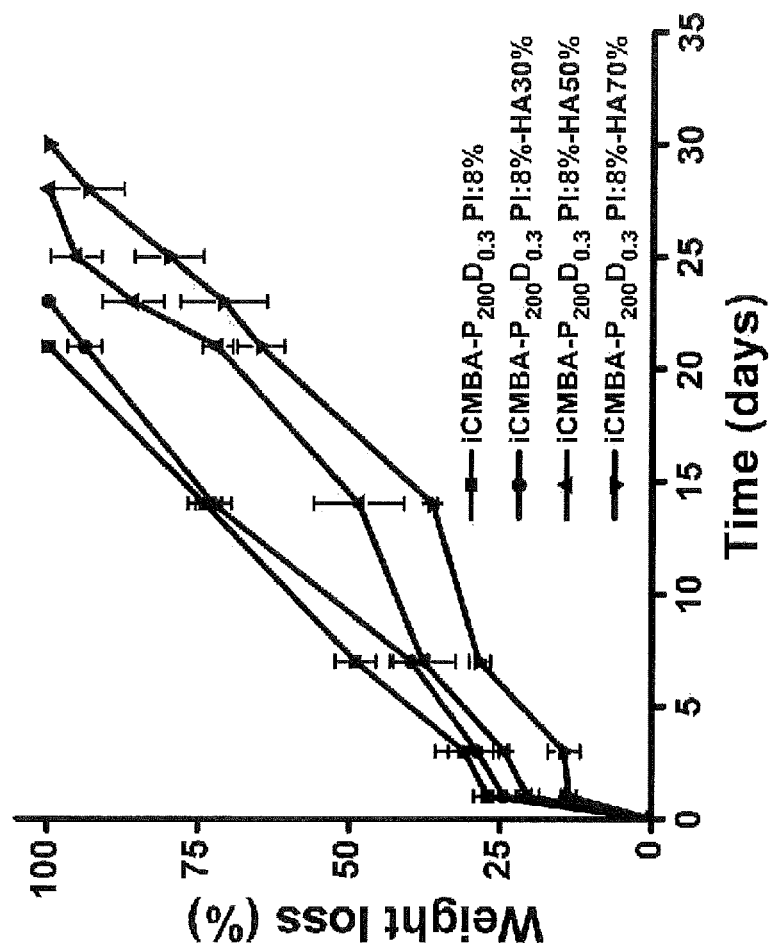
FIG. 10 illustrates some properties of composites according to some embodiments described herein.

Degradation studies were also conducted as described in Example 2. However, it should be noted that the degradation rate was based on the weight loss of iCMBA alone, which was measured by deducting the weight of the released HA from the total weight loss at each time point. The results are provided in FIG. 10.

EXAMPLE 6

Mineralization of Compositions

Compositions were mineralized according to some embodiments described herein as follows. Disk shaped scaffolds formed from a composite (iCMBA-$P_{200}D_{0.3}$ PI:8%-HA70%) prepared as described in Example 5 were immersed in simulated body fluid (SBF), which was prepared as described in Oyane et al., "Preparation and assessment of revised simulated body fluids," *Journal of Biomedical Materials Research Part A*, 2003; 65:188-95, the entirety of which is hereby incorporated by reference. To accelerate the mineralization process, concentrated SBF was used, in which the concentration of inorganic ions was five times that in human blood plasma (SBF-5×). The composite samples were immersed in 10 mL of SBF-5× and incubated at 37° C. for up to 5 days while the SBF was replaced every other day. At each predetermined time point the specimens (n=5) were taken out, gently washed with DI water to remove any soluble inorganic ions from the surface of samples, and air-dried. Next, the specimens were sputter-coated with silver and examined by scanning electron microscope (SEM) using a Hitachi 3000N instrument (Hitachi, Pleasanton, Calif.). The elemental analysis of the mineralized composites was also conducted by energy dispersive X-ray spectroscopy (EDX) to determine the composition and ratio of the elements present in the minerals formed on the composites surface. In addition to these composites, iCMBA-$P_{200}D_{0.3}$ PI:8% without HA was also subjected to mineralization as a control.

Figure 11:
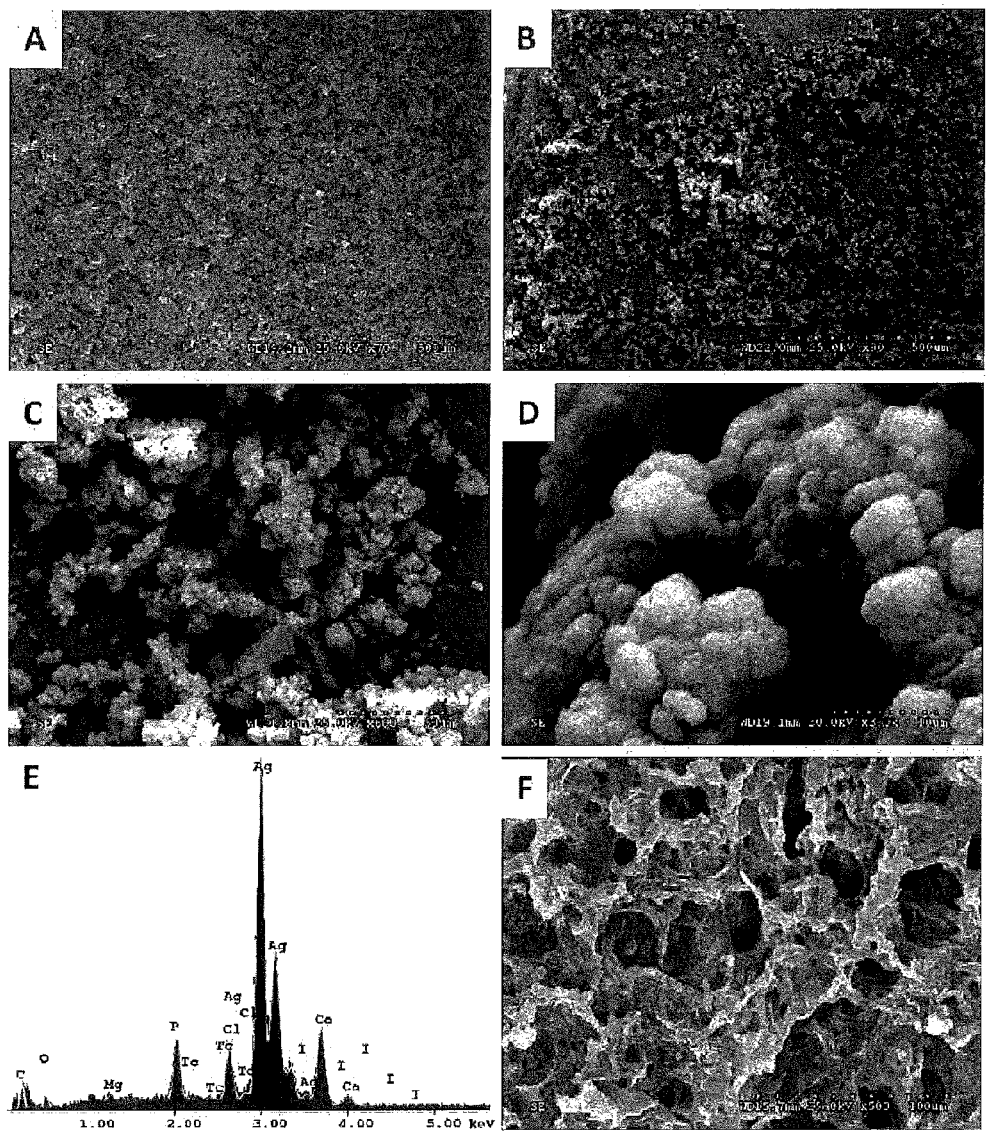
FIG. 11 illustrates the mineralization of composites according to some embodiments described herein.

After 1 day incubation in SBF-5×, no crystals on the surface of the samples were observed, as shown in FIG. 11A. As incubation continued, crystals of calcium phosphate began to form and grow. FIGS. 11B-D show the formation of the crystals on the surface of iCMBA-HA composite at 5 days. In addition, EDX analysis confirmed the existence of these crystals, in which the ratio of Ca/P was around 1.61 (FIG. 11E). In the case of the control samples, incubation in SBF-5× did not induce any crystal formation on the surfaces after 5 days (FIG. 11F).

EXAMPLE 7

In Vitro Biocompatibility

In vitro cell compatibility of composites according to some embodiments described herein was evaluated as follows.

Figure 12:
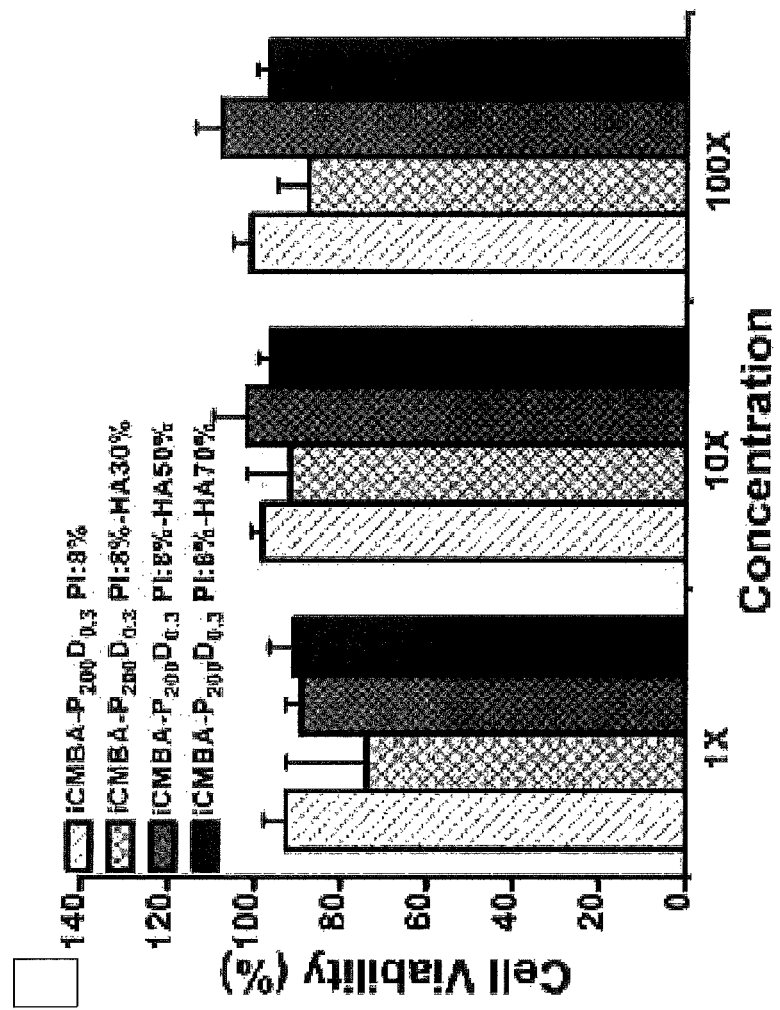
FIG. 12 illustrates the results of cytoxicity evaluations of compositions according to some embodiments described herein.

The cytotoxicity of the sol content or leachable fraction of some composites prepared according to Example 5 was assessed by incubating the composites for 24 hours in 5 mL of Minimum Essential Medium (MEM) Alpha cell culture medium (Invitrogen Corp, Eugene, Oreg.) containing 10% (v/v) fetal bovine serum (FBS) and 1% (v/v) streptomycin. Next, three different solutions were prepared for cell cultures: 1×, 10× and 100× (1× refers to a solution of leached products with no dilution; 10× and 100× refer to 10 times and 100 times dilution, respectively, of 1× with culture medium). To each well of a 96-well cell culture plate, 200 µL of solution of MC3T3 pre-osteoblast cells in complete MEM, with a concentration of $5\times10^4$ cells/mL, was added and incubated for 24 hours at 37° C., 5% $CO_2$ and 95% relative humidity. The medium of each well was then replaced by a MEM solution described above containing a composite described herein. Incubation was carried out for another 24 hours, followed by MTT assay analysis according to the manufacturer's protocol. The cytotoxicity of degradation products was also evaluated. Equal weights of some composites prepared according to Example 5 were fully degraded in 10 mL complete MEM Alpha cell culture medium. The resultant solutions were then diluted to three concentrations (1×, 10× and 100×) using MEM, and used for cell culture and subsequent MTT analysis. All of the above solutions were pH-neutralized and passed through a 0.2 µm filter prior to use for cell culture studies. The cell viability results were normalized to the viability of cells in blank medium. The results of the cytotoxicity evaluations of the soluble (leachable) content and the degradation products of various composites are shown in FIG. 12.

Figure 13:
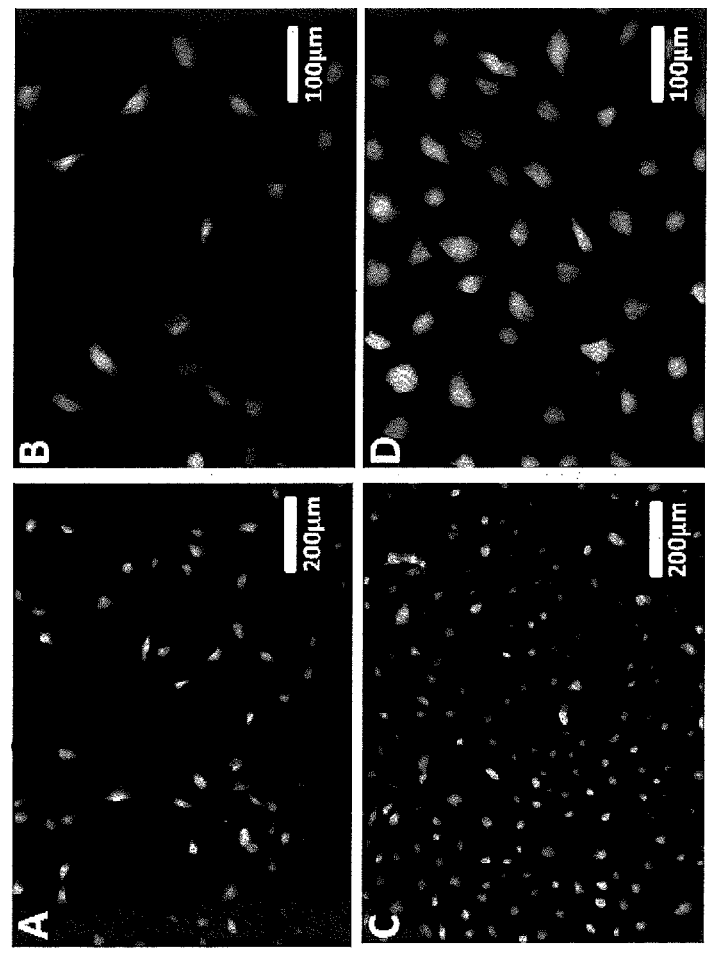
FIG. 13 illustrates the cell adhesion properties of composites according to some embodiments described herein.

The viability and adhesion of MC3T3 cells to the surface of composites described herein were also evaluated using fluorescence microscopy. Briefly, one drop of an iCMBA-HA composite (prior to completion of crosslinking) was uniformly spread on the surface of a glass slip cover and left to form a very thin layer of the composite. The sample was then sterilized by incubation in 70% ethanol for 24 hours followed by exposure to UV light for 3 hours. The sample was then placed in a 24-well plate and seeded by MC3T3 cells with a density of 50,000 cells/cm². At each time point (day 1 and day 3 post-seeding), the samples were removed from the well plate, rinsed by PBS and stained with CFDA-SE (carboxyfluorescein diacetate, succinimidyl ester) dye (Vybrant® CFDA SE Cell Tracer Kit, Invitrogen Corp, Eugene, Oreg.) according to the manufacturer's protocol. Next, the fluorescence microscopy images of stained samples were taken using a Nikon Eclipse Ti-U photomicroscope equipped with an Andor DR-328G camera (Nikon Instruments Inc, Melville N.Y.). The samples exhibited an excellent cell attachment to the composite films, as shown in FIG. 13. The proliferation of the cells was also observed throughout the two time points.

Figure 14:
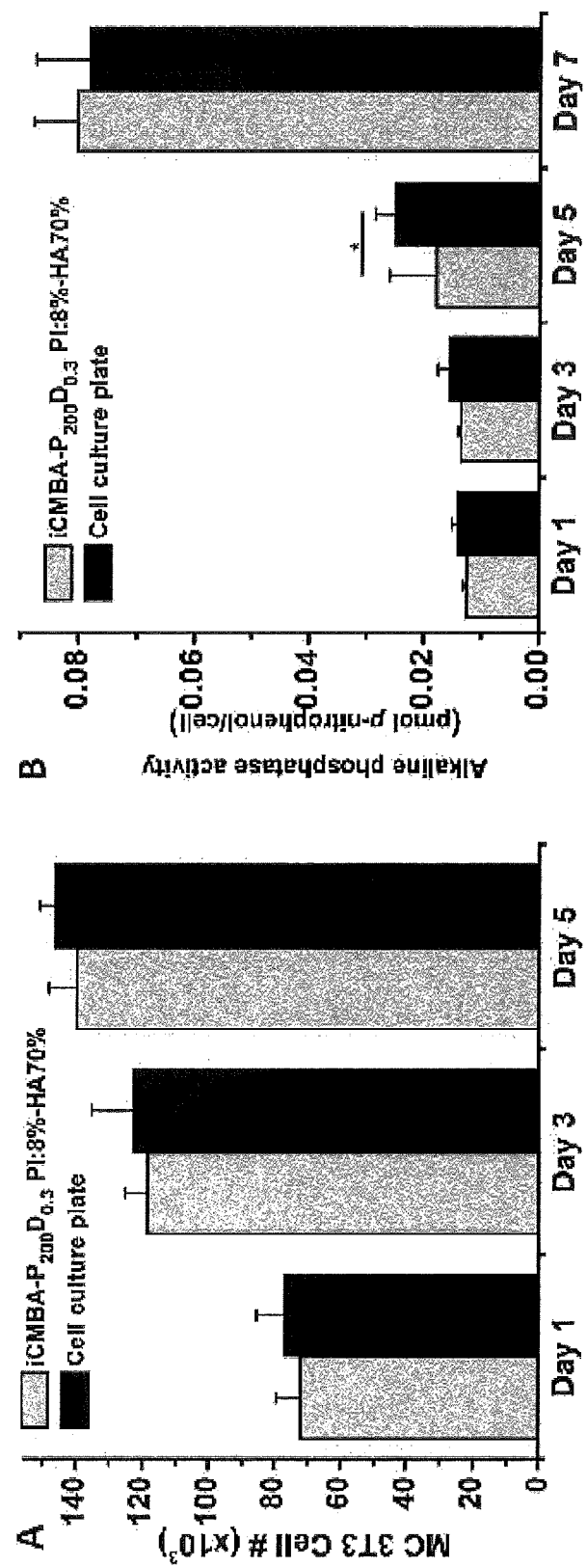
FIG. 14 illustrates in vitro evaluation results of composites according to some embodiments described herein.

The viability and proliferation of the cells seeded on the composite surfaces were further measured by DNA assay. For this purpose, the composite samples were cut into disk shapes to fit into the 24-well plate and sterilized by incubation in 70% ethanol for 24 hours, followed by exposure to UV light for 3 hours. MC3T3 cells were then seeded on the surface of the composites with a density of 50,000 cells/cm². At each time point (1 day, 3 days, and 5 days post-seeding), the samples were rinsed with TBS 1× (tris-buffered saline) and treated with 3 cycles of freeze-thaw sonication to break cells and expose their DNA. Quant-iT™ PicoGreen® dsDNA reagent (Invitrogen Corp, Eugene, Oreg.) was then used to quantify the double-stranded DNA through fluorescent staining and fluorescence excitation/emission at 480/520 nm. Using a known quantity of cells, a standard curve was prepared as a reference to correlate the fluorescence intensity to a number of cells. The results are shown in FIG. 14A. Seeding on a polystyrene cell culture plate was used as a control.

The differentiation of MC3T3 osteoblast precursor cells to osteoblasts was tracked by measuring the production of alkaline phosphatase (ALP) by osteoblasts. Cell-composite constructs were prepared as follows. Briefly, MC3T3 pre-osteoblast cells were cultured on sterile composite samples described herein, as well as on a cell culture plate as a control, with a concentration of 50,000 cells/cm². Then, 24 hours after seeding, the cell culture medium was replaced by a differentiation medium containing 50 µg ascorbic acid and 3.06 mg of beta-glycerol phosphate (BGP) in 1 mL of complete MEM medium. The differentiation medium was replaced every other day. At each time point (1, 3, 5, and 7 days post-seeding), the constructs were washed with PBS and treated with 3 freeze-thaw sonication cycles. ALP activity was then measured through incubation of 50 µL aliquots of homogenates with 4-nitrophenyl phosphate solution at 37° C. for 30 minutes. The amount of 4-nitrophenyl released due to the presence of ALP was then measured through absorption at 405 nm using spectrophotometer and by comparing to a standard curve of 4-nitrophenyl at various concentrations. ALP activity was normalized to the number of cells at each time point. The differentiation of MC3T3 pre-osteoblast cells to osteoblasts was evident from the ALP activity of osteoblast cells seeded on the composite samples, which increased from 0.0127 pmol p-nitrophenol/cell at day 1 to 0.0803 at day 7. The results are shown in FIG. 14B.

EXAMPLE 8

In Vivo Cell Evaluation

In vivo properties of compositions according to some embodiments described herein were evaluated as follows. All the materials and tools used were first sterilized by either passing through a 0.2 µm filter, for solutions, or autoclaving, for solids.

The composite used for the in vivo evaluation was iCMBA-$P_{200}$ $D_{0.3}$-HA70%. To prepare the composite, iCMBA-$P_{200}$ $D_{0.3}$ polymer or oligomer was first dissolved in water to achieve a 40% solution. A calculated amount of HA was then added followed by thorough mixing to reach a composition of 70% w/w of HA over the total dry composite weight. Next, the required amount of sodium periodate was added to achieve a PI-to-polymer or oligomer ratio of 6%. After vigorous mixing, the paste-like composite was injected into the area of interest as described below.

New Zealand Rabbits (male, average body weight 3 kilogram) were used as the animal model. All operations on the rabbits were carried out under general anesthesia, achieved with the intravenous injection of 3% pentobarbital sodium (30 mg per kilogram of body weight). The surgical areas were sterilized with 0.5% iodophor and then covered with a surgical towel to insure a clear operation field and to prevent incision infection. Before cutting skin, the fore limb of interest (the right side) was shaved to identify the radial head of the fore limb. A clear skin incision of 1.5 cm was made at the antero-lateral side of the radius, which was 1.5 cm distal to the radial head. The anterior surface of the right radius was exposed by intermuscular space, saving muscles and related tendons. To make a standard and reproducible comminuted radial facture, radial osteotomy was first performed at two sites with a surgical electric saw to produce a 1-cm-length bone block, and then the bone block was cut into several segments (usually 3-4 fragments) with bone rongeurs. A comminuted or multi-fragmentary fracture is a complex bone fracture in which the bone is fractured into several pieces. Before the radial osteotomy, the ulna was exposed and protected from fracture to provide sufficient biomechanical support for the fractured radius. After the comminuted fracture was created, several bone fragments were separated and the iCMBA-HA composite (at a gelled stage) was injected into the medullary space to unite the separate bone fragments. After ensuring that the injected composite united well with the bone fragments, the deep fascia was sutured with stitches as tightly as possible. After the skin was sutured, an external cast was provided to stabilize the radius after the operation. Cotton gauze was inserted between the skin and cast to keep the incision clean. All rabbits received buprenorphin (0.5 mg/kg) every 6 h for the first 3 postoperative days as analgesic therapy. Infection prophylaxis with penicillin (50000 U/kg) was maintained for the first 3 postoperative days twice a day. For control, the same procedure was repeated without using any composite or other bone-filling material. The animals were subjected to x-ray radiology and micro-CT testing at the 4th week after the operation to assess the bone tissue repair and regeneration through measuring bone mineral density (BMD) and the ratio of bone volume over tissue or total volume (BV/TV).

Figure 15:
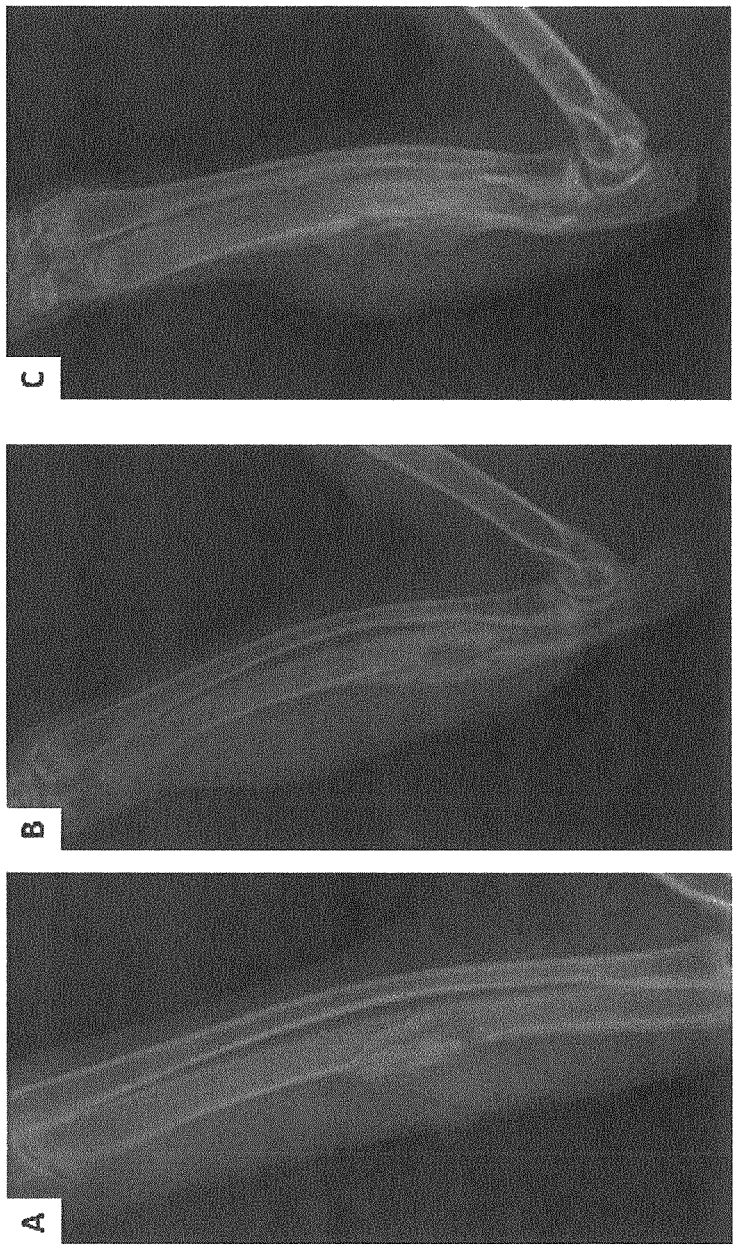
FIG. 15 illustrates a method of treatment according to one embodiment described herein.

The iCMBA-HA composite samples exhibited good flowability and were easy to inject. The set time was sufficiently long to allow the surgical procedure to be carried out as described above. FIG. 15 shows x-ray radiographs of the fractured bone right after fracture (A) and 4 weeks after treatment (B and C, wherein B=control and C=iCMBA-HA treatment). The bone treated with iCMBA-HA exhibited enhanced regeneration and healing of the fractured bone tissue compared to the control. In addition, the BMD and BV/TV for the composite-filled bone fracture were 388.4 mg/cc and 62,5%, respectively, which were significantly higher (p<0.05) than the control, which exhibited a BMD of 327.5 and a BV/TV of 49.3%.

EXAMPLE 9

Hydrogels

Hydrogels according to some embodiments described herein were prepared as follows. First, a series of polymers or oligomers denoted as iCMBA-$P_{200}$ $D_{0.3}$ was prepared as described in Example 1. Next, a series of hydrogels was prepared by dissolving the polymer or oligomer in water, followed by addition of a calculated amount of crosslinker initiator solution (PI in DI water) as described in Example 2. In addition, in some cases, the pH of the aqueous solution of polymer or oligomer was first altered to a value of 2.0, 5.0, or 7.0 by the dropwise addition of sodium hydroxide solution or hydrochloric acid.

Figure 16:
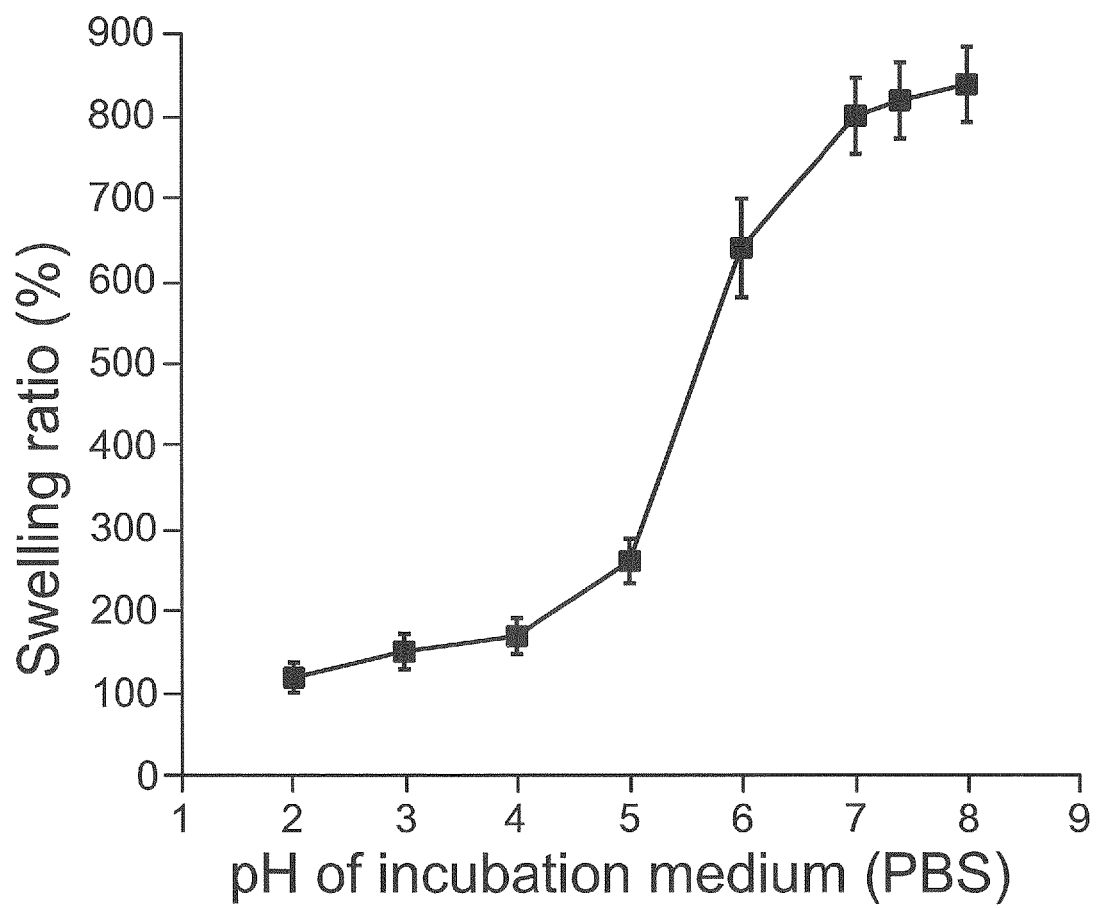
FIG. 16 illustrates some properties of crosslinked polymer networks according to some embodiments described herein.
Figure 17:
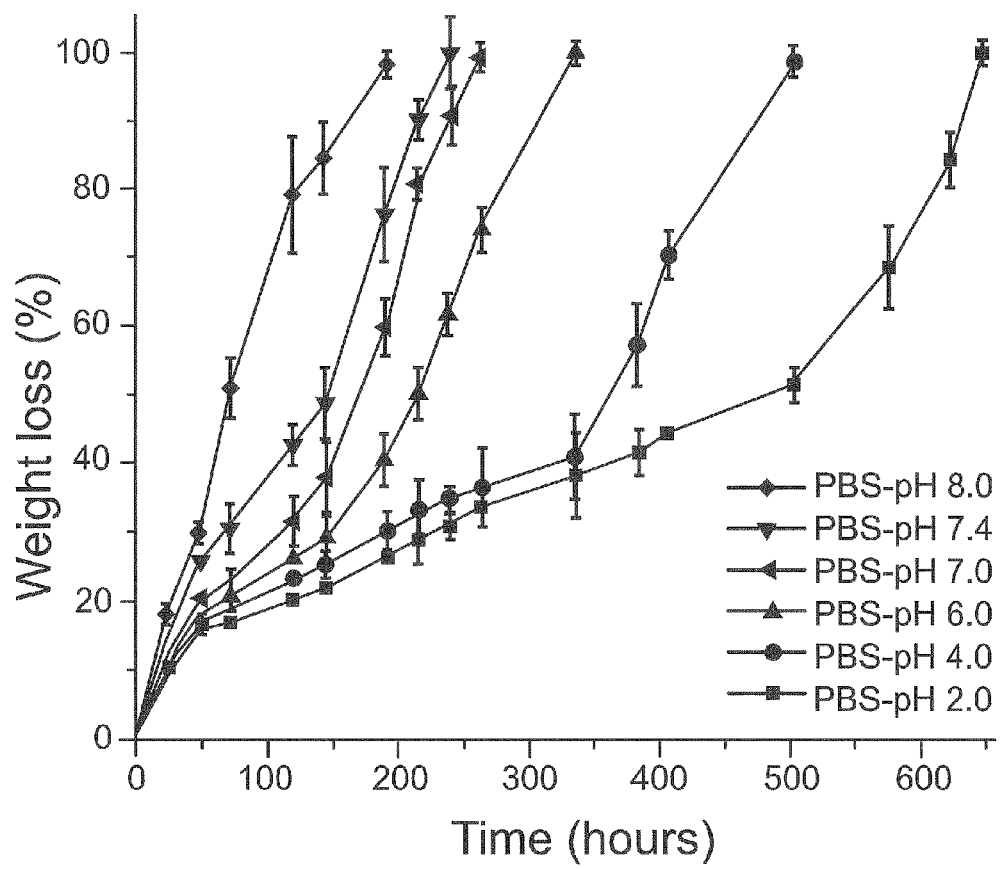
FIG. 17 illustrates some properties of crosslinked polymer networks according to some embodiments described herein.
Figure 18:
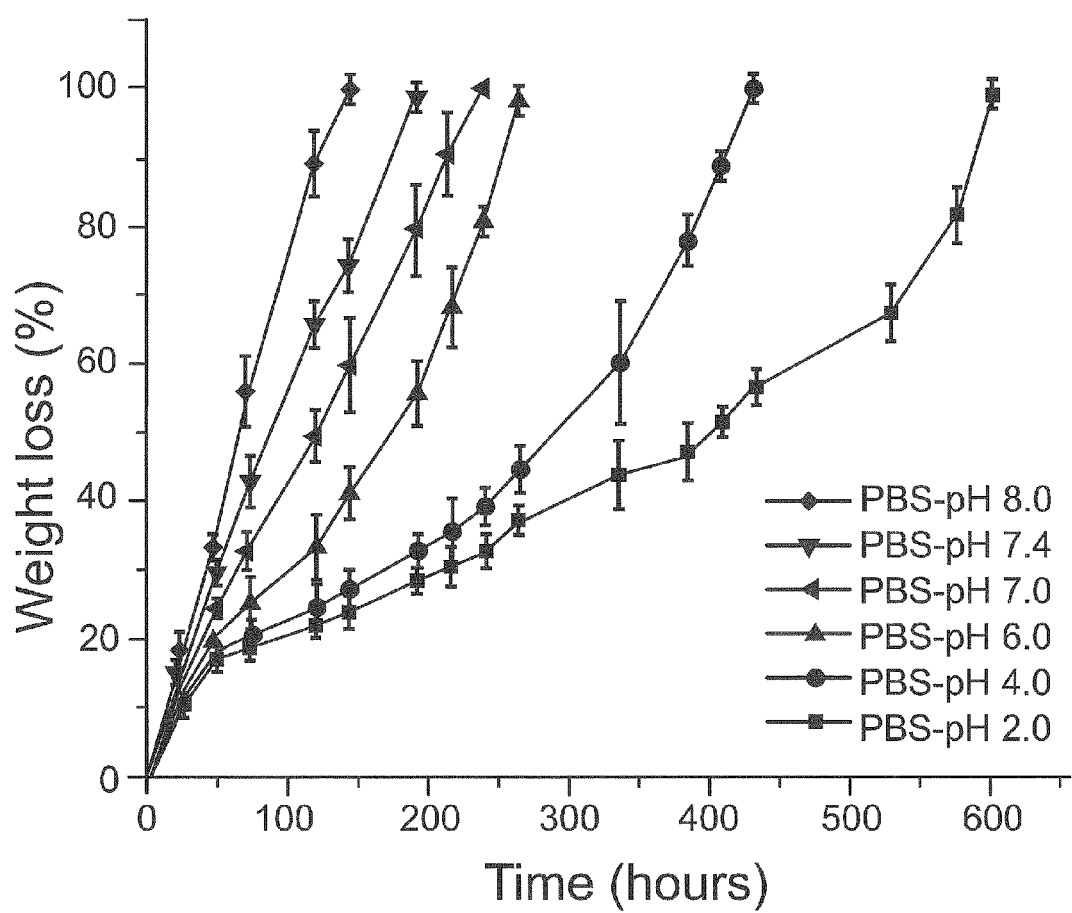
FIG. 18 illustrates some properties of crosslinked polymer networks according to some embodiments described herein.
Figure 19:
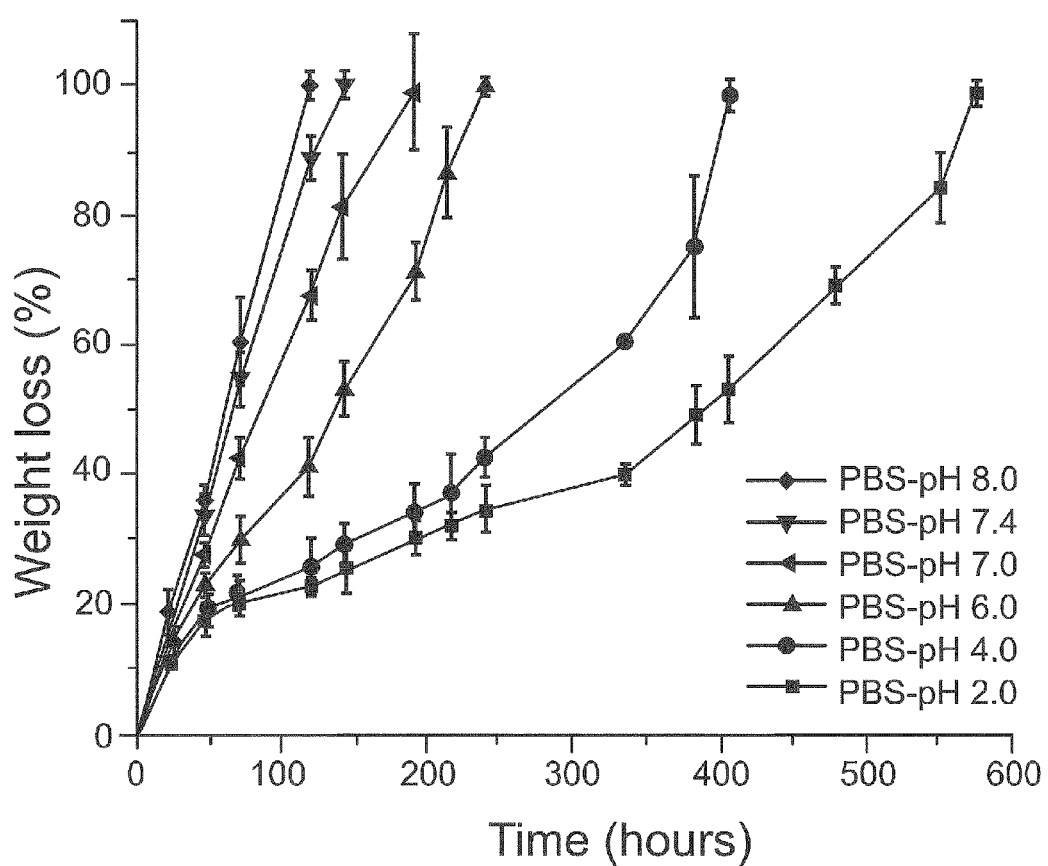
FIG. 19 illustrates some properties of crosslinked polymer networks according to some embodiments described herein.

The swelling ratio and degradation rate of crosslinked polymer networks were measured in PBS at different pH values (including 2.0, 4.0, 6.0, 7.0, 7.4, and 8.0) as described in Example 2. The swelling ratios for iCMBA-$P_{200}$ $D_{0.3}$ PI:8% is shown in FIG. 16. Degradation data for iCMBA-$P_{200}$ $D_{0.3}$ PI:4% is shown in FIG. 17 (polymer or oligomer pH of 2.0), FIG. 18 (polymer or oligomer pH of 5.0), and FIG. 19 (polymer or oligomer pH of 7.0).

Hydrogel network structure parameters were calculated using rubber elasticity theory. Specifically, equation (4) was used:

$$\tau = \frac{\rho RT}{\overline{M}_c}\left(1 - \frac{2\overline{M}_c}{\overline{M}_n}\right)\left(\alpha - \frac{1}{\alpha^2}\right)\left(\frac{v_{2,s}}{v_{2,r}}\right)^{1/3}, \quad (4)$$

where $\tau$ is the tensile stress applied to the hydrogel sample in the swollen state, $\rho$ is the density of the polymer (g/m$^3$), R is the universal gas constant (8.314 J/K·mol), T is the absolute experimental temperature, $M_c$ is the average molecular weight between two adjacent crosslinking points, $M_n$ is the number average molecular weight of the polymer, $\alpha$ is the extension ratio of the hydrogel, and $v_{2,s}$ and $v_{2,r}$ are the polymer volume fraction in the swollen state and the polymer volume fraction in the relaxed state (the relaxed state is defined as the state of the polymer immediately after crosslinking but before complete swelling), respectively.

In addition, the crosslinking density, $\rho_x$, was calculated using equation (5):

$$\rho_x = \frac{\rho}{M_c}, \quad (5)$$

where $\rho$ is the polymer density and $M_c$ is as described above.

All the experiments used to determine the various parameters of equations (4) and (5) were carried out at room temperature (23° C.). Matrix-assisted laser desorption/ionization mass spectroscopy (MALDI-MS) was used to measure the number average molecular weight of the iCMBA polymers or oligomers using a Shimadzu Biotech Axima Performance MALDI TOF-TOF mass spectrometer. N-diisopropylethylammonium α-cyano-3-hydroxycinnamate (CHCA-DIPEA) was used as the matrix to mix with the polymer or oligomer in a 1:10 polymer/oligomer:matrix molar ratio.

The polymer density was determined using two different techniques: liquid displacement and a geometric calculation based on the measured volume and weight of regular cylinder shaped specimens of the dry hydrogel. For the liquid displacement technique, the dry weight of a piece of crosslinked polymer network was measured. The polymer was then fully submerged in a graduate cylinder with a known volume of 1,4-dioxane. The volume of the polymer was then calculated by subtracting the initial volume of the liquid from its final volume. The density was then calculated by dividing the weight by the volume. The density determined from the geometric calculation was identical to that measured by liquid displacement.

The polymer volume fraction in the relaxed state, $v_{2,r}$, was calculated by dividing the polymer or oligomer volume over the total volume of polymer or oligomer plus the volume of the water in the polymer or oligomer solution and PI solution. The volume of the polymer or oligomer was calculated by dividing the weight of the polymer or oligomer by its density. To calculate the polymer volume fraction in the fully swollen state, $v_{2,s}$, the volume of the polymer or oligomer in the system was divided over the sum of the volume of the polymer or oligomer, the volume of water in the polymer or oligomer solution and PI solution, and the volume of absorbed water in the hydrogel. The weight of the water absorbed by the hydrogel in the fully swollen state was calculated by subtracting the weight of the hydrogel right after hydrogel formation from the weight of the fully swollen hydrogel. The calculated weight of absorbed water was then converted to volume by dividing it by the density of water. To determine the equilibrium or fully swollen state, the weight of the hydrogel was measured at different time points of incubating in water. The equilibrium state was considered the point when there was no further change in the weight of hydrogel. The total volume of the fully swollen hydrogel was also calculated using a liquid displacement method by measuring the increase in volume of water upon immersing the fully swollen hydrogel into a water-containing graduated cylinder. The difference between the calculated values using these two techniques was not significant.

The hydrogel in the fully swollen state was subjected to tensile test to determine the tensile stress (τ) and extension ratio (α) within the linear and elastic deformation region. The hydrogel samples were cut into 6 mm-wide specimens to that were pulled at the rate of 25.4 mm/min. using an MTS Insight 2 (MTS, Eden Prairie, Minn.). The tensile stress at 10% strain was recorded for the fully swollen sample. The extension ratio, α, was calculated from equation (6):

$$\alpha = \frac{L}{L0} = \text{strain} + 1, \quad (6)$$

where L and L0 are the elongated and initial length of the sample, respectively.

The network parameters of some hydrogels described herein are shown in Table 7. Both hydrogels in Table 7 are based on iCMBA-$P_{200}$ $D_{0.3}$. Hydrogel 1 was formed using 4% PI (w/w), and Hydrogel 2 was formed using 8% PI (w/w).

TABLE 7

Hydrogel network parameters.

| Hydrogel | MW of Polymer/ Oligomer | ρ (g/cm³) | $v_{2,s}$ | $v_{2,r}$ | $M_n$ (kDa) | α | $M_c$ (g/mol) | $\rho_x$ (mol/m³) |
|---|---|---|---|---|---|---|---|---|
| 1 | 1299.98 | 1.2503 ± 0.06 | 0.03425 | 0.2161 | 7.1 ± 1.9 | 1.1 | 643.48 | 1943.02 |
| 2 | 1299.98 | 1.2565 ± 0.04 | 0.04795 | 0.2167 | 24.4 ± 6.9 | 1.1 | 630.46 | 1992.99 |

EXAMPLE 10

Hydrogels Comprising Drugs

Figure 20:
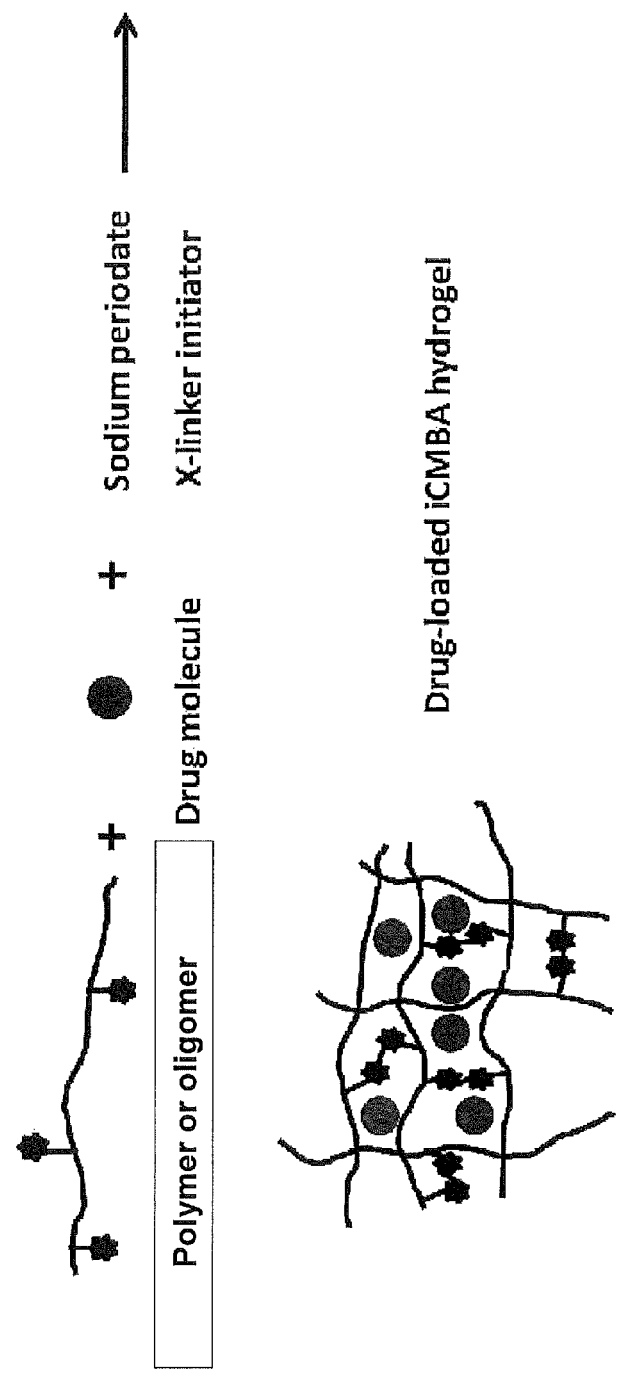
FIG. 20 illustrates a scheme of a method of making a composition according to one embodiment described herein.

Hydrogels according to some embodiments described herein were prepared as follows. To prepare a drug-loaded hydrogel, a measured amount of anti-cancer drug doxorubicin (DOX) was solubilized in a 50% w/w solution of a polymer or oligomer described herein in DI water, followed by vigorous mixing of the solution using a vortexer. The polymer or oligomer was prepared as described in Example 1. The total amount of the drug was 1% (w/w, based on the weight of the drug and the weight of the polymer or oligomer). Upon complete dissolution of DOX, a calculated amount of crosslinker solution (PI) was added to the mixture to form a crosslinked polymer network hydrogel. In some instances, the pH of the solution of polymer or oligomer was also varied, as described in Example 9. The DOX was encapsulated or entrapped in the crosslinked polymer network, as shown in FIG. 20.

Figure 21:
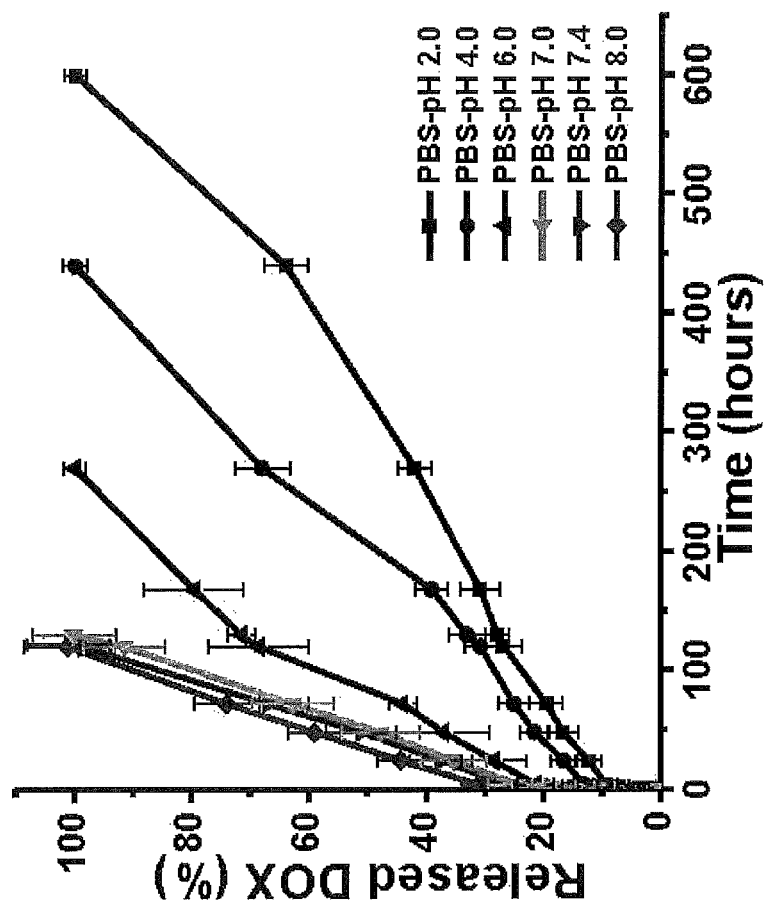
FIG. 21 illustrates some properties of hydrogels according to some embodiments described herein.
Figure 22:
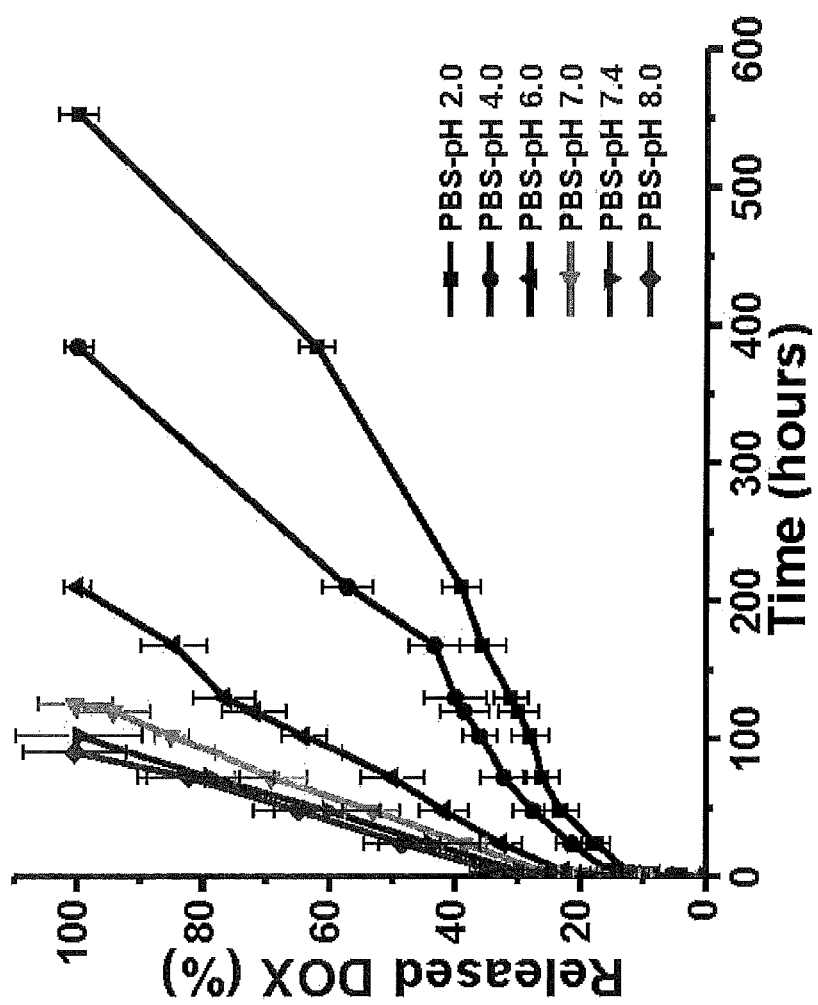
FIG. 22 illustrates some properties of hydrogels according to some embodiments described herein.
Figure 23:
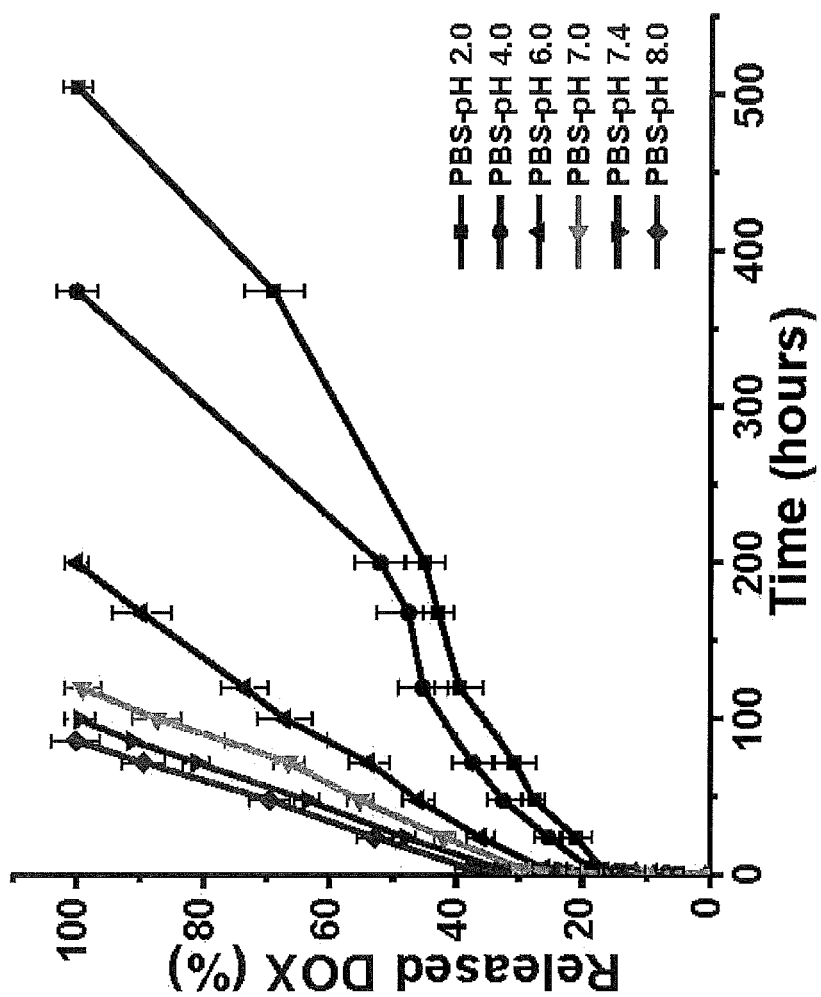
FIG. 23 illustrates some properties of hydrogels according to some embodiments described herein.

To evaluate the release rate of DOX from the hydrogel, the drug-loaded hydrogel was cut into a disk shape using a core borer, weighed, and incubated at 37° C. in PBS having various pHs ranging from 2 to 8. At each of several predetermined time points, the supernatant was removed and replaced with fresh PBS. The amount of drug released into the supernatant from the hydrogel was determined by fluorescence spectrometry. DOX is a fluorescent material with excitation in the range of 470-480 nm and emission in the range of 580-590 nm. For the evaluation, the excitation wavelength was 470 nm and the measured emission wavelength was 585 nm. To correlate the intensity of the fluorescence to the amount of DOX, a standard curve of the intensity versus known concentrations of the drug solution was prepared. The resulting polynomial equation (of order 3) was then used to convert the intensity of the DOX released from the hydrogel to a corresponding drug amount. The amount of drug released was calculated as a percentage of release over time, based on the total amount of drug initially present in the hydrogel. The cumulative drug release profiles of some hydrogels described herein (based on iCMBA-$P_{200}$ $D_{0.3}$) are shown in FIG. 21 (polymer or oligomer pH of 2.0), FIG. 22 (polymer or oligomer pH of 5.0), and FIG. 23 (polymer or oligomer pH of 7.0).

EXAMPLE 11

Compositions Comprising Nanoparticles

Compositions comprising nanoparticles according to some embodiments described herein were prepared as follows. Nanoparticles (NPs) of polymers or oligomers, polymer networks, or hydrogels described herein were prepared by first preparing a 1% or 0.5% solution of polymer or oligomer (iCMBA-$P_{200}$ $D_{0.3}$ made according to Example 1) in DI water. Next, the pH of the solution was brought to approximately 2.0 using hydrochloric acid, causing the solution to become a cloudy suspension. The cloudy suspension was then sonicated for 2 minutes at a power of 20 W using an Ultrasonic Homogenizer Model 300 VT (BioLogics Inc, Manassas, Va.). A calculated amount of crosslinker initiator (PI) solution described herein was then added under sonication. The mixture was sonicated for another 4 minutes at 40 W while in an ice bath. Next, the mixture was passed through a 0.2 μm filter and centrifuged at 15,000 rpm for 20 minutes to obtain the NPs. The size and size distribution of the NPs were measured by dynamic light scattering (DLS) using a ZetaPals machine (Brookhaven Instruments Corp, Novato, Calif.). For the DLS measurement, a dilute suspension of NPs in DI water (<0.1%) was prepared, transferred into a cuvette, and placed in the DLS instrument. The DLS measurement was conducted three times for each sample. When a 0.5% solution of NPs was used, the average diameter of the NPs was 244±56 nm. In the case of a 1% solution, the average size of was 327±83 nm.

The stability of the NPs was evaluated by measuring the zeta potential of the particles with a ZetaPals instrument equipped with zeta potential analysis software. For the measurement, the NPs were suspended in DI water and placed into a cuvette. The zeta potential of the NPs was approximately −29 mV.

EXAMPLE 12

Drug Release from Compositions Comprising Nanoparticles

Figure 24:
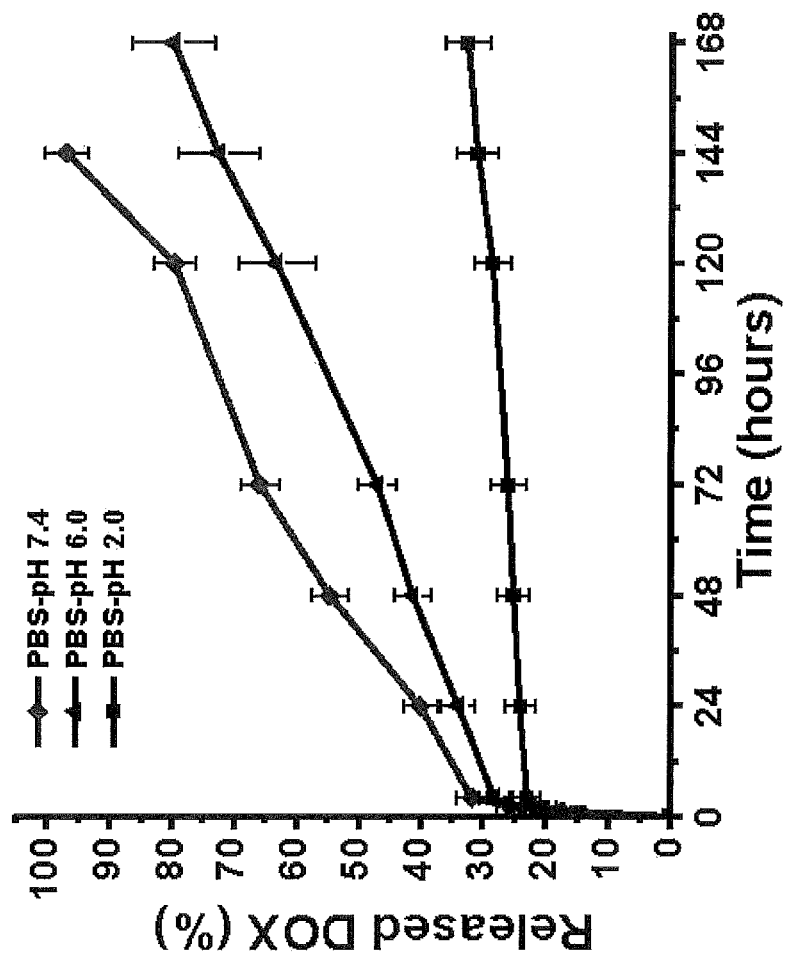
FIG. 24 illustrates a method of treatment according to one embodiment described herein.

The release of drugs from compositions comprising nanoparticles according to some embodiments described herein was evaluated as follows. To prepare NPs comprising drugs, a measured mass of NPs prepared according to Example 11 (with a polymer or oligomer pH of 2.0) was suspended in a known volume of a 1% solution of DOX in DI water. The mixture was stirred for 24 hours to allow loading of the drug into the NPs, followed by centrifugation at 15,000 rpm for 20 minutes. The resulting drug-loaded NPs were then collected and placed into a dialysis tube with a MWCO of 1000 Da and incubated in PBS at three different pH values (2.0, 6.0, and 7.4) at 37° C. At each of several predetermined time points, the medium was replenished and the drug release was measured by fluorescence spectrophotometer of the collected supernatants, as described in Example 10. The drug release results are shown in FIG. 24.

The initial drug loading efficiency of the nanoparticles was calculated by comparing the fluorescence intensity of the initial drug solution and the amount of drug in the supernatant after incubation using equation (7):

Efficiency=(Initial amount of drug−Amount of drug in the supernatant)/(Initial amount of thug)×100     (7).

The drug loading efficiency of the NPs was 47.1%.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A composition comprising:
a polymer or oligomer that is the polymerization or oligomerization product of one or more monomers of Formula (A), one or more monomers of Formula (B) or (B'), and one or more monomers of Formula (C):

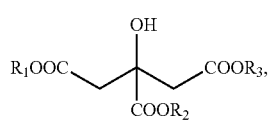

(A)

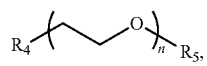

(B)

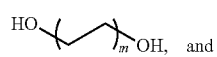

(B')

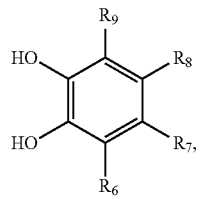

(C)

wherein
$R_1$, $R_2$, and $R_3$
  are independently —H, —CH$_3$, or —CH$_2$CH$_3$;
$R_4$ is —H, —OH, —OCH$_3$, —OCH$_2$CH$_3$, —CH$_3$, or —CH$_2$CH$_3$;
$R_5$ is —H, —CH$_3$, or —CH$_2$CH$_3$;
$R_6$, $R_7$, $R_8$, and $R_9$
  are independently —H, —CH$_2$(CH$_2$)$_x$NH$_2$, —CH$_2$(CHR$_{10}$)NH$_2$, or —CH$_2$(CH$_2$)$_x$COOH;
$R_{10}$ is —COOH or —(CH$_2$)$_y$COOH;
n and m
  are independently integers ranging from 1 to 20;
x is an integer ranging from 0 to 20; and
y is an integer ranging from 1 to 20;
wherein the polymer or oligomer is crosslinked to form a polymer network, wherein at least one crosslink in the crosslinked polymer or oligomer comprises two catechol moieties directly and covalently coupled to each other.

2. The composition of claim 1, wherein a monomer of Formula (C) comprises dopamine or L-DOPA.

3. The composition of claim 1 further comprising a particulate material mixed with the polymer or oligomer.

4. The composition of claim 1 further comprising a drug mixed with the polymer or oligomer.

5. The composition of claim 4, wherein the polymer or oligomer is in nanoparticulate form.

6. The composition of claim 1, wherein the polymer or oligomer is bonded to a surface.

7. A method of making a composition of claim 1 comprising:
providing a polycarboxylic acid of one or more monomers of Formula (A):

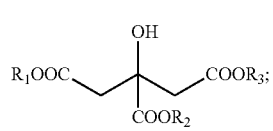

(A)

providing an alcohol of one or more monomers of Formula (B) or (B'):

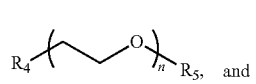

(B)

-continued

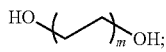
(B')

combining the polycarboxylic acid with the alcohol;
adding a catechol-containing species to the combination of the polycarboxylic acid and the alcohol, the catechol-containing species of one or more monomers of Formula (C):

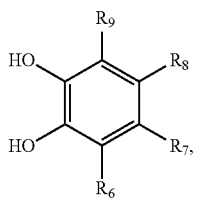
(C)

wherein
$R_1$, $R_2$, and $R_3$
  are independently —H, —$CH_3$, or —$CH_2CH_3$;
$R_4$ is —H, —OH, —$OCH_3$, —$OCH_2CH_3$, —$CH_3$, or —$CH_2CH_3$;
$R_5$ is —H, —$CH_3$, or —$CH_2CH_3$;
$R_6$, $R_7$, $R_8$, and $R_9$
  are independently —H, —$CH_2(CH_2)_xNH_2$, —$CH_2(CHR_{10})NH_2$, or —$CH_2(CH_2)_xCOOH$;
$R_{10}$ is —COOH or —$(CH_2)_yCOOH$;
n and m
  are independently integers ranging from 1 to 20;
x is an integer ranging from 0 to 20; and
y is an integer ranging from 1 to 20; and
forming a polymer or oligomer from the polycarboxylic acid, the alcohol, and the catechol-containing species, wherein the polymer or oligomer is crosslinked to form a polymer network, wherein at least one crosslink in the crosslinked polymer or oligomer comprises two catechol moieties directly and covalently coupled to each other.

8. The method of claim 7 further comprising adding a particulate material to the polymer or oligomer.

9. The method of claim 7 further comprising adding a drug to the polymer or oligomer.

10. The method of claim 7 further comprising forming nanoparticles of the polymer network.

11. A method of adhering biological tissue comprising:
disposing the composition of claim 1 between a first portion of biological tissue and
a second portion of biological tissue.

12. The method of claim 11 further comprising contacting the first portion of biological tissue with the second portion of biological tissue.

13. A method of treating disease comprising disposing the composition of claim 4 in a biological compartment.

14. The method of claim 13 further comprising releasing the drug of the composition into the biological compartment.

15. A method of promoting biological tissue growth comprising:
providing a scaffold comprising the composition of claim 3; and
disposing the scaffold in a tissue growth medium.

16. The composition of claim 3, wherein the particulate material is selected from the group consisting of hydroxyapatite, tricalcium phosphate, biphasic calcium phosphate, bioglass, ceramic, magnesium powder, magnesium alloy, and decellularized bone tissue particles.

17. A composition comprising:
a polymer or oligomer bonded to a surface of an inorganic material, wherein the polymer or oligomer is the polymerization or oligomerization product of one or more monomers of Formula (A), one or more monomers of Formula (B) or (B'), and one or more monomers of Formula (C):

(A)

(B)

(B')

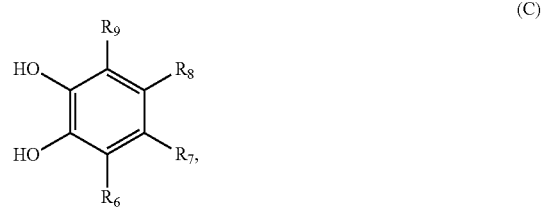
(C)

wherein
$R_1$, $R_2$, and $R_3$
  are independently —H, —$CH_3$, or —$CH_2CH_3$;
$R_4$ is —H, —OH, —$OCH_3$, —$OCH_2CH_3$, —$CH_3$, or —$CH_2CH_3$;
$R_5$ is —H, —$CH_3$, or $CH_2CH_3$;
$R_6$, $R_7$, $R_8$, and $R_9$
  are independently —H, —$CH_2(CH_2)_xNH_2$, —$CH_2(CHR_{10})NH_2$, or —$CH_2(CH_2)_xCOOH$;
$R_{10}$ is —COOH or —$(CH_2)_yCOOH$;
n and m
  are independently integers ranging from 1 to 20;
x is an integer ranging from 0 to 20; and
y is an integer ranging from 1 to 20;
wherein the polymer or oligomer is crosslinked to form a polymer network,
wherein at least one crosslink in the crosslinked polymer or oligomer comprises two catechol moieties directly and covalently coupled to each other, and
wherein the polymer or oligomer is bonded to the surface of the inorganic material.

18. The composition of claim 17, wherein a monomer of Formula (C) comprises dopamine or L-DOPA.

19. The composition of claim 17, wherein the polymer or oligomer is crosslinked to form a polymer network.

20. The composition of claim 19, wherein the polymer or oligomer is crosslinked through one or more catechol moieties.

21. The composition of claim 17, further comprising a particulate material mixed with the polymer or oligomer.

22. The composition of claim 21, wherein the particulate material is selected from the group consisting of hydroxyapatite, tricalcium phosphate, biphasic calcium phosphate, bioglass, ceramic, magnesium powder, magnesium alloy, and decellularized bone tissue particles.

23. The composition of claim 17, further comprising a drug mixed with the polymer or oligomer.

24. The composition of claim 17, wherein the inorganic material is a mineral or oxide material.

* * * * *